(12) United States Patent
Levade et al.

(10) Patent No.: US 10,918,737 B2
(45) Date of Patent: Feb. 16, 2021

(54) METHODS AND PHARMACEUTICAL COMPOSITION FOR THE TREATMENT OF CANCER

(71) Applicants: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR); CENTRE HOSPITALIER UNIVERSITAIRE DE TOULOUSE, Toulouse (FR)

(72) Inventors: Thierry Levade, Toulouse (FR); Bruno Segui, Toulouse (FR); Nicolas Meyer, Toulouse (FR); Céline Colacios Viatgé, Toulouse (FR); Nathalie Andrieu-Abadie, Toulouse (FR); Florie Bertrand, Toulouse (FR)

(73) Assignees: INSERM (Institut National de la Santé et de la Recherche Médicale), Paris (FR); Université Paul Sabatier Toulouse III, Toulouse (FR); Centre Hospitalier Universitaire de Toulouse, Toulouse (FR)

( * ) Notice: Subject to any disclaimer, the term of this patent is extended or adjusted under 35 U.S.C. 154(b) by 211 days.

(21) Appl. No.: 16/073,141
(22) PCT Filed: Jan. 27, 2017
(86) PCT No.: PCT/EP2017/051844
§ 371 (c)(1),
(2) Date: Jul. 26, 2018
(87) PCT Pub. No.: WO2017/129790
PCT Pub. Date: Aug. 3, 2017

(65) Prior Publication Data
US 2019/0038763 A1 Feb. 7, 2019

(30) Foreign Application Priority Data
Jan. 28, 2016 (EP) .................................. 16305085
May 27, 2016 (EP) .................................. 16305613
Jul. 26, 2016 (EP) .................................. 16305962

(51) Int. Cl.
*A61P 35/00* (2006.01)
*A61K 47/68* (2017.01)
*C07K 16/24* (2006.01)
*C07K 16/28* (2006.01)
*A61K 39/395* (2006.01)
*A61K 39/00* (2006.01)
*A61K 45/06* (2006.01)

(52) U.S. Cl.
CPC .... *A61K 47/6845* (2017.08); *A61K 39/39558* (2013.01); *A61P 35/00* (2018.01); *C07K 16/241* (2013.01); *C07K 16/2818* (2013.01); *C07K 16/2878* (2013.01); *A61K 45/06* (2013.01); *A61K 2039/507* (2013.01); *A61K 2039/57* (2013.01); *C07K 2317/31* (2013.01)

(58) Field of Classification Search
CPC ... A61P 35/00; A61K 47/6845; A61K 16/241; A61K 2039/507
USPC ............................................ 424/133.1, 136.1
See application file for complete search history.

(56) References Cited

U.S. PATENT DOCUMENTS

2019/0031756 A1* 1/2019 Levade .......... C12Y 301/04012
2019/0031757 A1* 1/2019 Levade .................. A61P 35/00
2019/0353657 A1* 11/2019 Osman ............. A61K 39/39558

FOREIGN PATENT DOCUMENTS

| WO | 2007/056540 A2 | 5/2007 |
| WO | 2011/159877 A2 | 12/2011 |
| WO | 2015/187359 A1 | 12/2015 |
| WO | 2016/023875 A1 | 2/2016 |

OTHER PUBLICATIONS

Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*
De Corte, et al. (patentepi.org/issue 1 (2019).*
Marco Donia et al: "The controversial role of TNF in melanoma", Oncoimmunolgy, vol. 5, No. 4, Oct. 29, 2015, p. e1107699.

* cited by examiner

*Primary Examiner* — Lynn A Bristol
(74) *Attorney, Agent, or Firm* — W & C IP

(57) ABSTRACT

The present invention relates to methods and pharmaceutical composition for the treatment of cancer. In particular, the present invention relates to a method for enhancing the potency of an immune checkpoint inhibitor administered to a subject as part of a treatment regimen for cancer, the method comprising: administering a pharmaceutically effective amount of a TNFα blocking agent to a subject in combination with the immune checkpoint inhibitor.

8 Claims, 12 Drawing Sheets

METHODS AND PHARMACEUTICAL COMPOSITION FOR THE TREATMENT OF CANCER

FIELD OF THE INVENTION

Figure 1:
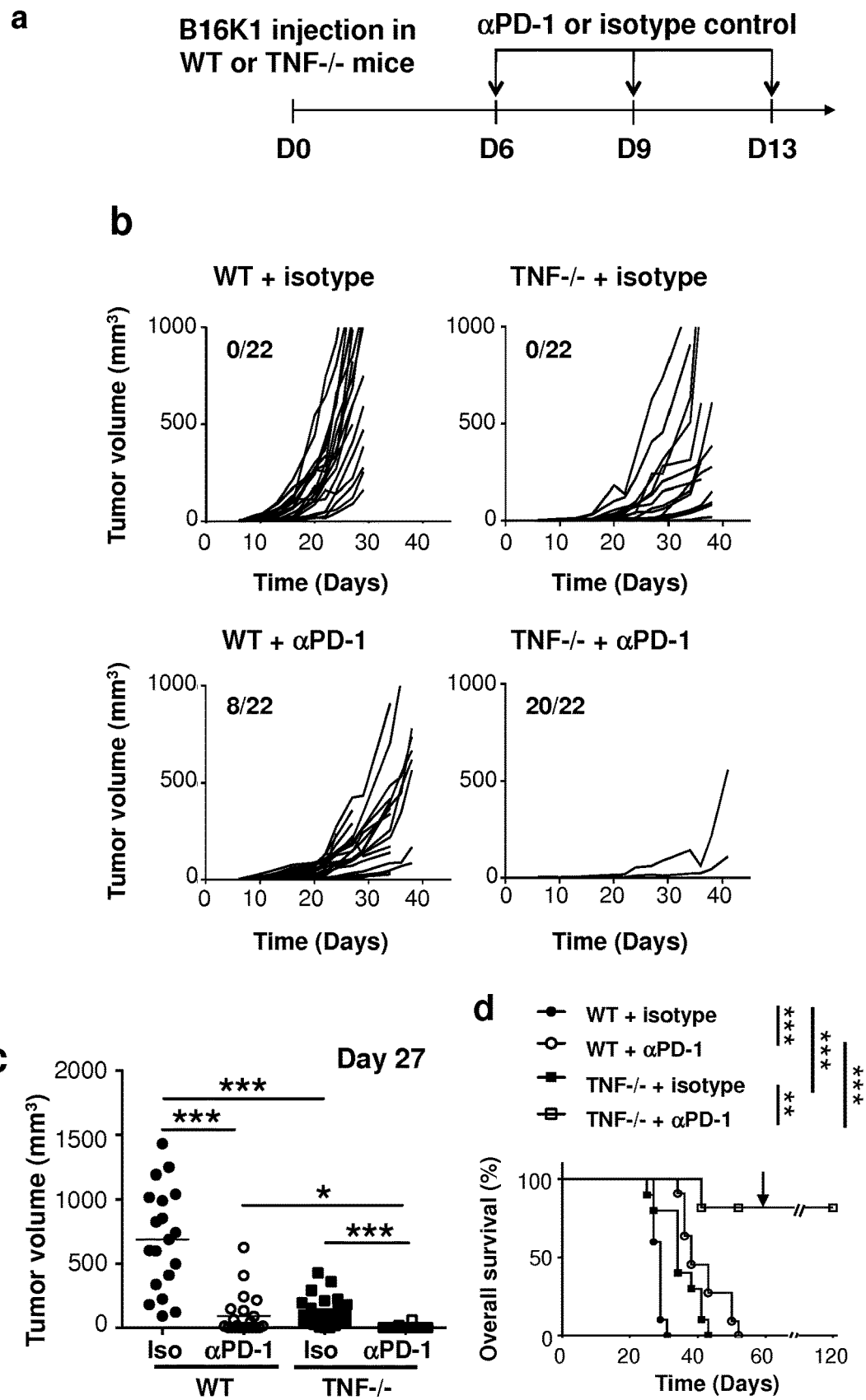

The present invention relates to methods and pharmaceutical composition for the treatment of cancer.

BACKGROUND OF THE INVENTION

Immune checkpoints such as Cytotoxic T Lymphocyte Antigen-4 (CTLA-4) and Programmed-cell death 1 (PD-1) are key negative regulators of anti-cancer immune response, limiting lymphocyte activation and facilitating tumor cell immune escape and cancer progression. Monoclonal antibodies inhibiting CTLA-4 (ipilimumab, tremelimumab) or PD-1 (nivolumab, pembrolizumab) have demonstrated significant efficacy in the treatment of metastatic melanoma, promoting high response rate and long-lasting tumor control (Márquez-Rodas I, Ann Transl Med. 2015; 3(18):267). Despite promising results, about 40% of patients do not display therapeutic response and a significant proportion of responders experience tumor relapse in the 2 years following treatment induction. It was recently demonstrated that host TNF-R1-dependent TNF signaling impairs CD8+ T cell-dependent immune response against melanoma (Bertrand et al., Cancer Research, 2015; 75(13):2619-28). TNF blockade (using Etanercept) or deficiency (TNF knock out mice) facilitates the accumulation of CD8+ Tumor-Infiltrating Lymphocytes (TILs), thereby limiting the growth of mouse melanoma cell lines (B16K1 and Yumm), which express Major Histocompatibility Class I molecules (MHC-I) at high levels. Similar findings were observed in mice lacking TNF-R1, but not TNF-R2, indicating that host TNF-R1 plays a critical role in limiting the establishment of such a CD8+ T cell-dependent immune response against melanoma under our experimental conditions. In terms of molecular mechanism, TNF-R1 likely behaves as a novel immune checkpoint by triggering cell death of activated CD8+ T cells. This conclusion is supported by the following findings that (i) naive CD8+ T cells, which expressed TNF-R2 but not TNF-R1, resisted TNF-induced cell death; (ii) activated CD8+ T cells, which significantly expressed TNF-R1, were sensitive to exogenous TNF; and (iii) TNF-R1-deficient CD8+ T cells were fully resistant to TNF-induced cell death. The role of TNF-R1 as an immune checkpoint in melanoma gets further credence as illustrated by our data showing that the accumulation of activated CD8+ T cells into melanoma was facilitated by TNF-R1 deficiency in an adoptive transfer experiment performed in CD8-deficient hosts (Bertrand et al., Cancer Research, 2015; 75(13):2619-28). Therefore EP14305687 discloses that anti-TNF or anti-TNF-R1 neutralizing molecules could be used in humans for treating advanced melanoma.

SUMMARY OF THE INVENTION

The present invention relates to methods and pharmaceutical composition for the treatment of cancer. In particular the present is defined by the claims.

DETAILED DESCRIPTION OF THE INVENTION

Tumor necrosis Factor α (TNF) plays a dual role in oncoimmunology[1,2], either acting as an anti-cancer factor[3,4], or behaving as an immunosuppressor cytokine[5-10] and limiting CD8+ Tumor-infiltrating lymphocytes (TILs)[1,2,11]. Emerging immunotherapies targeting immune checkpoints, like anti-PD-1, have radically changed our strategy to fight melanoma[12]. However, 60-67% of patients does not respond to anti-PD-1[13,34], and good responders develop severe immune-related adverse events with a frequency of 11.7-13.3%[13,14], which can be cured by anti-TNF[15]. The consequences of TNF blockade on the anti-cancer immune response triggered by anti-PD-1 remain unknown. Herein, the inventors show that TNF/TNFR1 deficiency or blockade synergized with anti-PD-1 in the treatment of experimental melanoma, leading to frequent total tumor regression and greatly improving overall survival. TNF or TNFR1 deficiency also sensitized Lewis lung carcinoma to anti-PD-1. Mechanistically, TNF that was produced upon anti-PD-1 potently induced the expression of TIM-3 on CD8+ and CD4+ TILs, a key regulator of T cell exhaustion and an immune-checkpoint involved in melanoma resistance or escape to anti-PD-1[16]. Consequently, TNF blockade prevented TIM-3 upregulation and dramatically enhanced IFNγ production and CD8+ TIL content. This preclinical study demonstrates that anti-TNF and anti-PD-1 synergize on anti-cancer immune response. In the present invention, TNFα blocking agent is not administered for treating enterocolitis, colitis or for improving tolerability or maintaining efficacy of PD-L1 antibody in combination with antibody activating CD40.

Accordingly, the present invention relates to a method for enhancing the potency of an immune checkpoint inhibitor administered to a subject as part of a treatment regimen for cancer, the method comprising: administering a pharmaceutically effective amount of a TNFα blocking agent to a subject in combination with the immune checkpoint inhibitor.

A further object of the present invention relates to a method of treating cancer in a subject in need thereof comprising administering to the subject a therapeutically effective combination of an immune checkpoint inhibitor with a TNFα blocking agent, wherein administration of the combination results in enhanced therapeutic efficacy relative to the administration of the immune checkpoint inhibitor alone.

A further object of the present invention relates to a method of treating cancer in a subject in need thereof comprising administering to the subject a therapeutically effective combination of an immune checkpoint inhibitor with a TNFα blocking agent.

In some embodiments, the method of the invention comprises administering to the subject a therapeutically effective combination of a TNFα blocking agent with an anti-CTLA-4 antibody and a PD-1 inhibitor such as anti-PD1 antibody and anti-PDL1 antibody.

In some embodiments, the method of the invention does not comprise administering the combination of a TNFα blocking agent, a PD-L1 antibody and an antibody activating CD40 (TNFR).

The term "CD40" has its general meaning in the art and refers to CD40, the member of the tumor necrosis factor receptor (TNFR) superfamily, a regulator of the anti-tumor immune response via its expression on antigen presenting cells (APCs) that include B lymphocytes, dendritic cells (DCs), and monocytes (Grewal I S et al, Ann Rev Immunol, 1998; 16: 111-35; Van Kooten C et al, Leukoc. Biol, 2000; 67:2-17; O'Sullivan B et al, Crit Rev Immunol. 2003; 23(1 2):83-107). The term "antibody activating CD40" refers to antibodies activating CD40 as described in WO2016/

023875. In some embodiments, the subject suffers from a cancer. As used herein, the term "cancer" has its general meaning in the art and includes, but is not limited to, solid tumors and blood-borne tumors. The term cancer includes diseases of the skin, tissues, organs, bone, cartilage, blood and vessels. The term "cancer" further encompasses both primary and metastatic cancers. Examples of cancers that may be treated by methods and compositions of the invention include, but are not limited to, cancer cells from the bladder, blood, bone, bone marrow, brain, breast, colon, esophagus, gastrointestinal tract, gum, head, kidney, liver, lung, nasopharynx, neck, ovary, prostate, skin, stomach, testis, tongue, or uterus. In some embodiments, the subject suffers from a cancer selected from the group consisting of Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangio sarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant, Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplasia, Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, non-small cell lung cancer (NSCLC) which coexists with chronic obstructive pulmonary disease (COPD), Ocular oncology, Oligoastrocytoma, Oligodendroglioma, Oncocytoma, Optic nerve sheath, meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastema, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute, lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, the subject suffers from melanoma. As used herein, "melanoma" refers to a condition characterized by the growth of a tumor arising from the melanocytic system of the skin and other organs. Most melanocytes occur in the skin, but are also found in the meninges, digestive tract, lymph nodes and eyes. When melanoma occurs in the skin, it is referred to as cutaneous melanoma. Melanoma can also occur in the eyes and is called ocular or intraocular melanoma. Melanoma occurs rarely in the meninges, the digestive tract, lymph nodes or other areas where melanocytes are found. In some embodiments, the melanoma is a metastatic melanoma. 40-60% of melanomas carry an activating mutation in the gene encoding the serine-threonine protein kinase B-RAF (BRAF). Among the BRAF mutations observed in melanoma, over 90% are at codon 600, and among these, over 90% are a single nucleotide mutation resulting in substitution of valine for glutamic acid (BRAFV600E). In some embodiments, the subject suffers from a melanoma resistant to BRAF inhibitors. As used herein, the term "resistant" refers to the repeated outbreak of melanoma, or a progression of the melanoma independently of whether the disease was cured before said outbreak or progression. As used herein, the term "BRAF inhibitor" refers to an agent that is capable of inhibiting BRAF kinase or mutated BRAF kinase activity (one or more mutated forms of serine-threonine protein kinase B-RAF (BRAF)) (e.g. BRAFV600E). Accordingly, the term "BRAF inhibitors" encompasses within its scope a compound that is capable of inhibiting BRAF or its mutated form; or a compound that is capable of inhibiting V600 mutated form of BRAF. Examples of BRAF inhibitors include but are not limited to BAY43-9006 (sorafenib, Bayer), vemurafenib (PLX4032, Plexxikon; RG7204, RO5185426, Hofmann-LaRoche), GDC-0879 (GlaxoSmithKline), dabrafenib (GSK21 18436, GlaxoSmithKline), PLX4720 (Hofmann-LaRoche), BMS-908662 (XL281, Bristol-Myers Squibb), LGX818 (Novartis), PLX3603 (R05212054, Hofmann-LaRoche), ARQ-736 (ArQule), DP-4978 (Decipher) or RAF265 (Novartis).

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein the term "immune checkpoint protein" has its general meaning in the art and refers to a molecule that is expressed by T cells in that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489). Examples of inhibitory checkpoint molecules include A2AR, B7-H3, B7-H4, BTLA, CTLA-4, CD277, IDO, KIR, PD-1, LAG-3, TIM-3 and VISTA. The Adenosine A2A receptor (A2AR) is regarded as an important checkpoint in cancer therapy because the tumor microenvironment has relatively high levels of adenosine, which lead to a negative immune feedback loop through the activation of A2AR. B7-H3 or CD276 was originally understood to be a co-stimulatory molecule but is now regarded as co-inhibitory. B7-H4 or VTCN1, which is expressed by tumor cells and tumor-associated macrophages, plays a role in tumour escape. BTLA (B and T Lymphocyte Attenuator) or CD272, is a ligand for TNF receptor superfamily member 14 or HVEM (Herpes Virus Entry Mediator). Whereas cell surface expression of BTLA is gradually downregulated during differentiation of human CD8+ T cells from the naive to effector cell phenotype, tumor-specific human CD8+ T cells express high levels of BTLA. CTLA-4 (Cytotoxic T-Lymphocyte-Associated protein 4) or CD152, which is expressed on Treg cells, regulates T cell proliferation. IDO (Indoleamine 2,3-dioxygenase) is a tryptophan catabolic enzyme and a related immune-inhibitory protein. IDO is known to suppress T and NK cells, generate and activate Tregs and myeloid-derived suppressor cells, and promote tumor angiogenesis. Another important molecule is also TDO (tryptophan 2,3-dioxygenase). KIR (Killer-cell Immunoglobulin-like Receptor) is a receptor for MHC Class I molecules on NK cells. LAGS (Lymphocyte Activation Gene-3) suppresses the immune response through its effect on Tregs as well as its direct effects on CD8+ T cells. PD-1 (Programmed Death 1) receptor, which has two ligands, PD-L1 and PD-L2, is the target of Merck & Co.'s melanoma drug Keytruda. It gained FDA approval in September 2014. Targeting PD-1 can restore immune function in the tumor microenvironment. TIM-3 (T-cell Immunoglobulin domain and Mucin domain 3) is expressed on activated human CD4+ T cells and regulates Th1 and Th17 cytokines. TIM-3 acts as a negative regulator of Th1/Tc1 function by triggering cell death upon interaction with its ligand, galectin-9. VISTA (V-domain Ig suppressor of T cell activation) is primarily expressed on hematopoietic cells so that consistent expression of VISTA on leukocytes within tumors may allow VISTA blockade to be effective across a broad range of solid tumors. As used herein, the term "TIM-3" has its general meaning in the art and refers to T cell immunoglobulin and mucin domain-containing molecule 3. The natural ligand of TIM-3 is galectin 9 (Gal9). As used herein, the term "PD-1" has its general meaning in the art and refers to programmed cell death protein 1 (also known as CD279). PD-1 acts as an immune checkpoint, which upon binding of one of its ligands, PD-L1 or PD-L2, inhibits the activation of T cells.

As used herein, the term "immune checkpoint inhibitor" has its general meaning in the art and refers to any compound inhibiting the function of an immune inhibitory checkpoint protein. Inhibition includes reduction of function and full blockade. Preferred immune checkpoint inhibitors are antibodies that specifically recognize immune checkpoint proteins. A number of immune checkpoint inhibitors are known and in analogy of these known immune checkpoint protein inhibitors, alternative immune checkpoint inhibitors may be developed in the (near) future. The immune checkpoint inhibitors include peptides, antibodies, nucleic acid molecules and small molecules. In particular, the immune checkpoint inhibitor of the present invention is administered for enhancing the proliferation, migration, persistence and/or cytoxic activity of CD8+ T cells in the subject and in particular the tumor-infiltrating of CD8+ T cells of the subject. As used herein "CD8+ T cells" has its general meaning in the art and refers to a subset of T cells, which express CD8 on their surface. They are MHC class I-restricted, and function as cytotoxic T cells. "CD8+ T cells" are also called cytotoxic T lymphocytes (CTL), T-killer cell, cytolytic T cells or killer T cells. CD8 antigens are members of the immunoglobulin superfamily and are associative recognition elements in major histocompatibility complex class I-restricted interactions. The ability of the immune checkpoint inhibitor to enhance CD8+ T cell killing activity may be determined by any assay well known in the art. Typically said assay is an in vitro assay wherein CD8+ T cells are brought into contact with target cells (e.g. target cells that are recognized and/or lysed by CD8+ T cells). For example, the immune checkpoint inhibitor of the present invention can be selected for the ability to increase specific lysis by CD8+ T cells by more than about 20%, preferably with at least about 30%, at least about 40%, at least about 50%, or more of the specific lysis obtained at the same effector: target cell ratio with CD8+ T cells or CD8 T cell lines that are contacted by the immune checkpoint inhibitor of the present invention, Examples of protocols for classical cytotoxicity assays are conventional. In some embodiments, the immune checkpoint inhibitor is a PD-1 inhibitor. As used herein the term "PD-1 inhibitor" as used herein refers to a compound, substance or composition that can inhibit the function of PD-1. For example, the inhibitor can inhibit the expression or activity of PD-1, modulate or block the PD-1 signaling pathway and/or block the binding of PD-1 to PD-L1 or PD-L2. In some embodiments, the immune checkpoint inhibitor is an antibody selected from the group consisting of anti-CTLA4 antibodies, anti-PD1 antibodies, anti-PDL1 antibodies, anti-PDL2 antibodies anti-TIM-3 antibodies, anti-LAGS antibodies, anti-B7H3 antibodies, anti-B7H4 antibodies, anti-BTLA antibodies, and anti-B7H6 antibodies.

Thus the expression "enhancing the potency of an immune checkpoint" refers to the ability of the TNFα blocking agent to increase the ability of the immune checkpoint inhibitor to enhance the proliferation, migration, persistence and/or cytoxic activity of CD8+ T cells. As used herein, the expression "enhanced therapeutic efficacy", relative to cancer refers to a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the patient according to any clinically acceptable criteria, including, for example, decreased tumor size, an increase in time to tumor progression, increased progression-free survival, increased overall survival time, an increase in life expectancy, a decrease of immune-adverse effects or an improvement in quality of life. In particular, "improved" or "enhanced" refers to an improvement or enhancement of 1%, 5%, 10%, 25% 50%, 75%, 100%, or greater than 100% of any clinically acceptable indicator of therapeutic outcome or efficacy. As used herein, the expression "relative to" when used in the context of comparing the activity and/or efficacy of a combination composition comprising the immune checkpoint inhibitor with the TNFα blocking agent to the activity and/or efficacy of the immune checkpoint alone, refers to a comparison using amounts known to be comparable according to one of skill in the art.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP404,097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference. In some embodiments, the antibody comprises human heavy chain constant regions sequences but will not deplete CD8+ T cells to which they are bound and preferably do not comprise an Fc portion that induces antibody dependent cellular cytotoxicity (ADCC). As used herein, the term "depleting", with respect to CD8+ T cells means a process, method, or compound that can kill, eliminate, lyse or induce such killing, elimination or lysis, so as to negatively affect the number of CD8+ T cells present in a sample or in a subject. The terms "Fc domain," "Fc portion," and "Fc region" refer to a C-terminal fragment of an antibody heavy chain, e.g., from about amino acid (aa) 230 to about aa 450 of human gamma heavy chain or its counterpart sequence in other types of antibody heavy chains (e.g., $\alpha$, $\delta$, $\epsilon$ and $\mu$ for human antibodies), or a naturally occurring allotype thereof. Unless otherwise specified, the commonly accepted Kabat amino acid numbering for immunoglobulins is used throughout this disclosure (see Kabat et al. (1991). Sequences of Protein of Immunological Interest, 5th ed., United States Public Health Service, National Institute of Health, Bethesda, Md.). In some embodiments the antibody of the present invention does not lead, directly or indirectly, to the depletion of CD8+ T cells (e.g. do not lead to a 10%, 20%, 50%, 60% or greater elimination or decrease in number CD8+ T cells). In some embodiments, the antibody of the present invention does not comprise an Fc domain capable of substantially binding to a FcgRIIIA (CD16) polypeptide. In some embodiments, the antibody of the present invention lacks an Fc domain (e.g. lacks a CH2 and/or CH3 domain) or comprises an Fc domain of IgG2 or IgG4 isotype. In some embodiments, the antibody of the present invention consists of or comprises a Fab, Fab', Fab'-SH, F (ab') 2, Fv, a diabody, single-chain antibody fragment, or a multispecific antibody comprising multiple different antibody fragments. In some embodiments, the antibody of the present invention is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551 by Idusogie et al.

Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CTLA-4 antibody is tremelimumab, (ticilimumab, CP-675, 206). In some embodiments, the anti-CTLA-4 antibody is ipilimumab (also known as 10D1, MDX-D010) a fully human monoclonal IgG antibody that binds to CTLA-4. Examples of PD-1 and PD-L1 antibodies are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699. In some embodiments, the PD-1 blockers include anti-PD-L1 antibodies. In certain other embodiments the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade. Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207:2187-94). Antibodies having specificity for TIM-3 are well known in the art and typically those described in WO2011155607, WO2013006490 and WO2010117057. In some embodiments, the immune checkpoint inhibitor is an IDO inhibitor. Examples of IDO inhibitors are described in WO 2014150677. Examples of IDO inhibitors include without limitation 1-methyl-tryptophan (IMT), β-(3-benzofuranyl)-alanine, β-(3-benzo(b)thienyl)-alanine), 6-nitro-tryptophan, 6-fluoro-tryptophan, 4-methyltryptophan, 5-methyl tryptophan, 6-methyl-tryptophan, 5-methoxy-tryptophan, 5-hydroxy-tryptophan, indole 3-carbinol, 3,3'-diindolylmethane, epigallocatechin gallate, 5-Br-4-Cl-indoxyl 1,3-diacetate, 9-vinylcarbazole, acemetacin, 5-bromo-tryptophan, 5-bromoindoxyl diacetate, 3-Amino-naphtoic acid, pyrrolidine dithiocarbamate, 4-phenylimidazole a brassinin derivative, a thiohydantoin derivative, a β-carboline derivative or a brassilexin derivative. Preferably the IDO inhibitor is selected from 1-methyl-tryptophan, β-(3-benzofuranyl)-alanine, 6-nitro-L-tryptophan, 3-Amino-naphtoic acid and β-[3-benzo(b)thienyl]-alanine or a derivative or prodrug thereof.

As used herein, the term "TNFα" or "TNF-alpha" denotes the tumor necrosis factor—alpha. The human TNF-alpha is a human cytokine encoded by the TNF-alpha gene. As used herein, the term "TNFα blocking agent" or "TBA", it is herein meant a biological agent which is capable of neutralizing the effects of TNFα. Said agent is a preferentially a protein such as a soluble TNFα receptor, e.g. Pegsunercept, or an antibody. In some embodiments, the TBA is a monoclonal antibody having specificity for TNFα or for TNFα receptor. In some embodiments, the TBA is selected in the group consisting of Etanercept (Enbrel®), Infliximab (Remicade®), Adalimumab (Humira®), Certolizumab pegol (Cimzia®), and golimumab (Simponi®). Recombinant TNF-receptor based proteins have also been developed (e.g. etanercept, a recombinant fusion protein consisting of two extracellular parts of soluble TNFα receptor 2 (p75) joined by the Fc fragment of a human IgG1 molecule). A pegylated soluble TNF type 1 receptor can also be used as a TNF blocking agent. Additionally, thalidomide has been demonstrated to be a potent inhibitor of TNF production. TNFα blocking agents thus further include phosphodiesterase 4 (IV) inhibitor thalidomide analogues and other phosphodiesterase IV inhibitors. As used herein, the term "etanercept" or "ETA" denotes the tumor necrosis factor—alpha (TNFα) antagonist used for the treatment of rheumatoid arthritis. The term "etanercept" (ETA, ETN, Enbrel) is a recombinant TNF-receptor IgG-Fc-fusion protein composed of the p75 TNF receptor genetically fused to the Fc domain of IgG1. Etanercept neutralizes the proinflammatory cytokine tumor necrosis factor-α (TNFα) and lymphotoxin-α (Batycka-Baran et al., 2012).

A further object relates to a method of preventing tumor escape in a subject treated with a PD-1 inhibitor comprising administering to the subject a therapeutically effective amount of a TNFα blocking agent.

As used herein, the term "tumor escape" refers to any mechanism by which tumors escape the host's immune system. In some embodiments, the method is particularly suitable for preventing tumor escape induced by the expression of TIM-3. In some embodiments, the method is particularly suitable for preventing tumor escape induced by the expression of TIM-3 and PD-1. In some embodiments, the method is particularly suitable for preventing tumor escape induced by the expression of TIM-3 and PD-L1. In some embodiments, the method comprises i) determining the expression level of TIM-3 in a tumor tissue sample obtained from the subject, iii) comparing the expression level determined at step i) with a predetermined reference value and iv) co-administering to the subject a therapeutically effective amount of a PD-1 inhibitor and a TNFα blocking agent. As used herein, the term "tumor tissue sample" has its general meaning in the art and encompasses pieces or slices of tissue that have been removed including following a surgical tumor resection. The tumor tissue sample can be subjected to a variety of well-known post-collection preparative and storage techniques (e.g., fixation, storage, freezing, etc.) prior to determining the cell densities. The tumor tissue sample can be used in microarrays, called as tissue microarrays (TMAs). The expression of TIM-3 is typically determined by immunohistochemistry, immunofluorescence or any method capable of determining the expression level of mRNA encoding for TIM-3.

As used herein the term "co-administering" as used herein means a process whereby the combination of the TNFα blocking agent and the immune checkpoint inhibitor, is administered to the same patient. The TNFα blocking agent and the immune checkpoint inhibitor may be administered simultaneously, at essentially the same time, or sequentially. The TNFα blocking agent and the immune checkpoint inhibitor need not be administered by means of the same vehicle. The TNFα blocking agent and the immune checkpoint inhibitor may be administered one or more times and the number of administrations of each component of the combination may be the same or different. In addition, the TNFα blocking agent and the immune checkpoint inhibitor need not be administered at the same site.

As used herein, the term "therapeutically effective combination" as used herein refers to an amount or dose of a TNFα blocking agent together with the amount or dose of the immune checkpoint inhibitor that is sufficient to treat the disease (i.e. cancer). The amount of the TNFα blocking agent in a given therapeutically effective combination may be different for different individuals and different tumor types, and will be dependent upon the one or more additional agents or treatments included in the combination. The "therapeutically effective amount" is determined using procedures routinely employed by those of skill in the art such that an "improved therapeutic outcome" results. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

A further object of the present invention relates to a method of treating cancer in a subject in need thereof comprising administering to the subject a therapeutically effective combination of a multispecific antibody comprising at least one binding site that specifically binds to an immune checkpoint protein (e.g., a PD-1 molecule), and at least one binding site that specifically binds to TNFα or a receptor for TNFα (TNFR1 or TNFR2).

Exemplary formats for the multispecific antibody molecules of the present invention include, but are not limited to (i) two antibodies cross-linked by chemical heteroconjugation, one with a specificity to the immune checkpoint protein (e.g. PD-1) and another with a specificity to TNFα or a receptor for TNFα (TNFR1 or TNFR2); (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivaient bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies. In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is a antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is a antibody of the present invention and the second antibody has a different binding specificity, or vice versa. The reducing conditions may, for example, be provided by adding a reducing agent, e.g. selected from 2-mercaptoethylamine, dithiothreitol and tris (2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety.

According to the invention, the active agent (e.g. TNFα blocking agent, the immune checkpoint inhibitor or the multispecific antibody) are administered to the subject in the form of a pharmaceutical composition. Typically, the active agent is combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The active agent can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1: Tumorigenesis in anti-PD-1-injected wild-type and TNF-deficient mice with established melanoma. C57BL/6 wild-type and TNF KO mice were intradermally and bilaterally grafted with $3 \times 10^5$ B16K1 melanoma cells before intraperitoneal injection of anti-PD-1 antibodies (αPD-1, 10 mg/Kg) or a relevant isotype control at the indicated days (n=11 mice per group). a, Scheme representing the experimental protocol. b and c, Tumor volumes were determined with a calliper at the indicated days. Individual curves are depicted for each tumor (b). Numbers indicate the tumor regression out of total tumors (b, insert). Values determined at day 27 for individual tumors are depicted. Bars represent mean values±sem (*$p<0.05$; $p<0.01$; *$p<0.001$) (c). d, Cumulative survival curves ($p<0.01$; *$p<0.001$).

Figure 2:
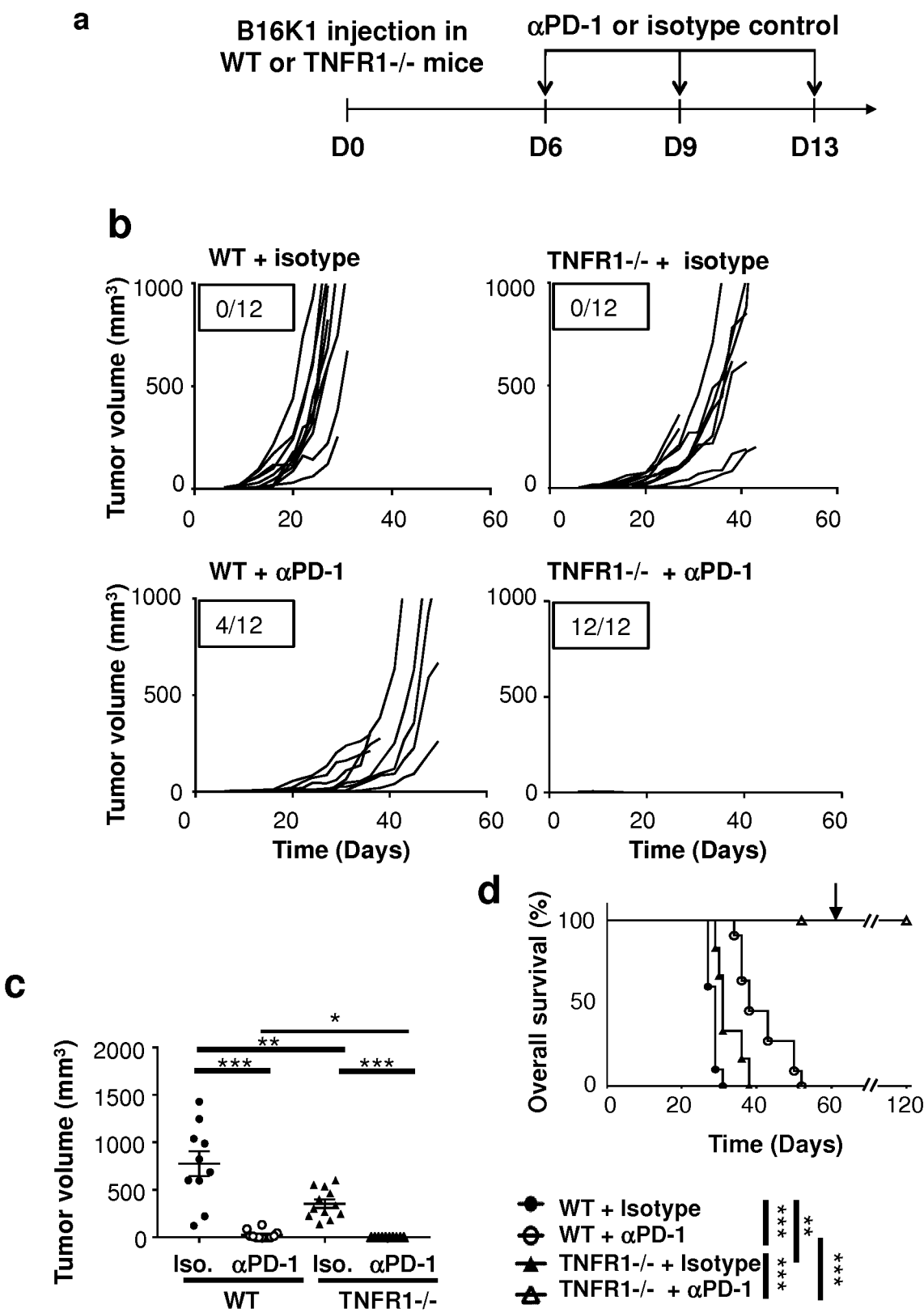

FIG. 2: Tumorigenesis in anti-PD-1-injected wild-type and TNF-R1-deficient mice with established melanoma. C57BL/6 wild-type and TNF-R1 KO mice were intradermally and bilaterally grafted with $3 \times 10^5$ B16K1 melanoma cells before intraperitoneal injection of anti-PD-1 antibodies (αPD-1, 10 mg/Kg) or a relevant isotype control at the indicated days (n=6 mice per group). A, Scheme representing the experimental protocol. B and C, Tumor volumes were determined with a calliper at the indicated days. Individual curves are depicted for each tumor (B). Numbers indicate the tumor regression out of total tumors (B, insert). Values determined at day 27 for individual tumors are depicted. Bars represent mean values±sem (*$p<0.05$; $p<0.01$; *$p<0.001$) (C). D, Cumulative survival curves ($p<0.01$; *$p<0.001$).

Figure 3:
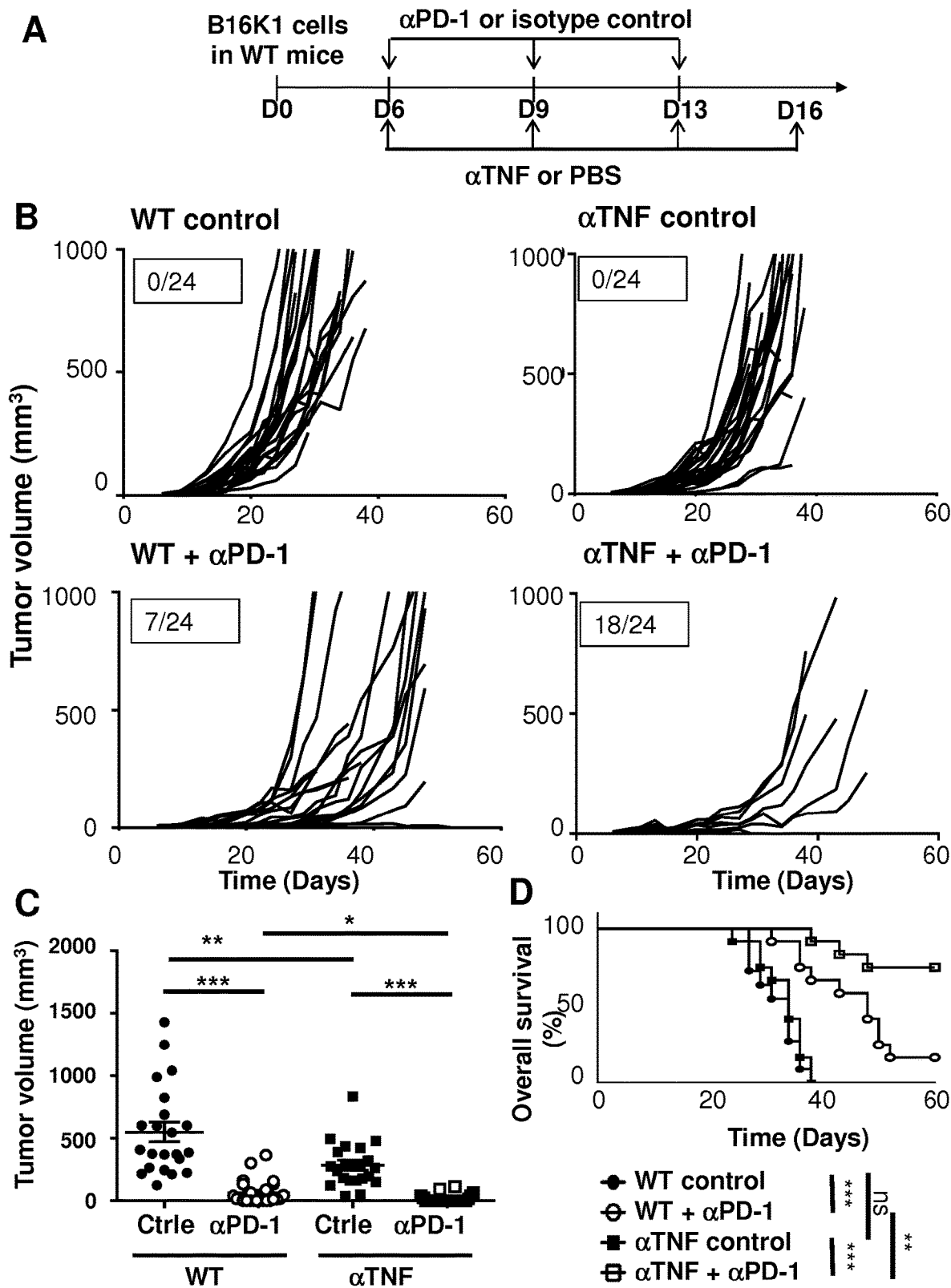

FIG. 3: Anti-PD-1 and anti-TNF injection in WT mice with established melanoma. C57BL/6 wild-type mice were intradermally and bilaterally grafted with $3 \times 10^5$ B16K1 melanoma cells before intraperitoneal injection of anti-PD-1 and/or anti-TNF antibodies or a relevant isotype control (10 mg/Kg for each antibody) at the indicated days (n=12 mice per group). A, Scheme representing the experimental protocol. B and C, Tumor volumes were determined with a calliper at the indicated days. Individual curves are depicted for each tumor (B). Numbers indicate the tumor regression out of total tumors (B, insert). Values determined at day 27 for individual tumors are depicted. Bars represent mean values±sem (*$p<0.05$; $p<0.01$; *$p<0.001$) (C). D, Cumulative survival curves ($p<0.01$; *$p<0.001$; ns $p>0.5$).

Figure 4:
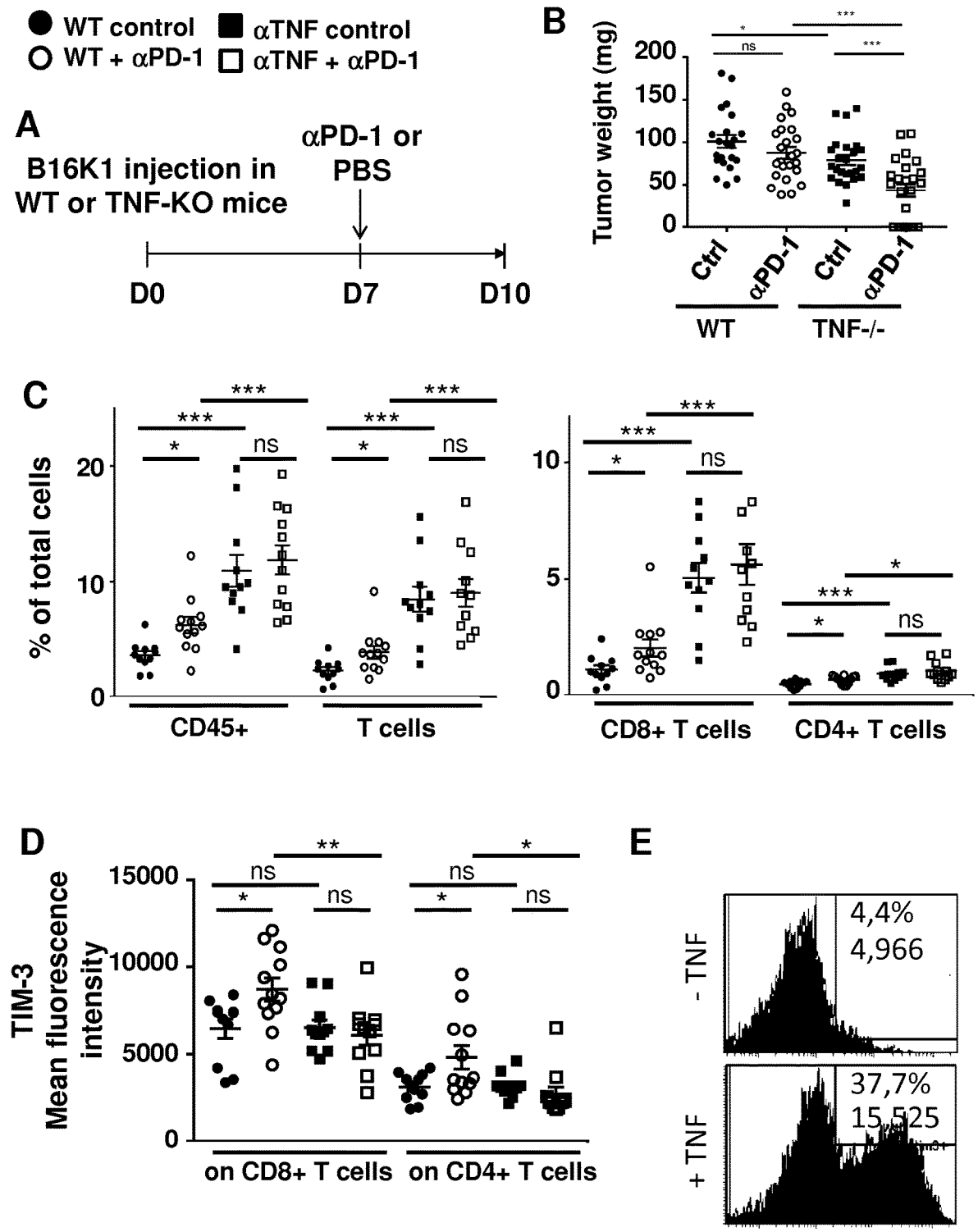

FIG. 4: Immune cell infiltration in tumors from anti-PD-1 injected wild-type and TNF-deficient mice with established melanoma. C57BL/6 wild-type and TNF-KO mice were intradermally and bilaterally grafted with $1 \times 10^6$ B16K1 melanoma cells before intraperitoneal injection of anti-PD-1 antibodies (αPD-1, 10 mg/Kg) or vehicle (PBS) at day 7. A, Scheme representing the experimental protocol. B, At day 10, mice were sacrificed and tumors were weighed. Data are means±sem of at least 22 tumors per group. (ns: $p>0.5$, *: $p<0.05$; ***$p<0.001$). C, Tumors were dissociated and TIL content analysis was performed by using flow cytometry. The proportion of total CD45+, Thy1+, CD4+ and CD8+ TILs was determined. Data are means±sem of at least 11 tumors per group. (ns: $p>0.05$, *: $p<0.05$; ***$p<0.001$). D, The mean of fluorescence intensity of TIM-3 staining on CD8+ TILs and CD4+ TILs was determined by flow cytometry. Data are means±sem of at least 11 tumors per group. E, CD8 T cells were purified from wild-type spleen and activated prior to incubation with 6 ng/mL TNF for 3 days. TIM-3 expression was next analysed by flow cytometry. Values indicate % of TIM-3 positive cells and mean of fluorescence intensity of TIM-3 staining (ns: p>0.05, *: p<0.05; **: p<0.01).

Figure 5:
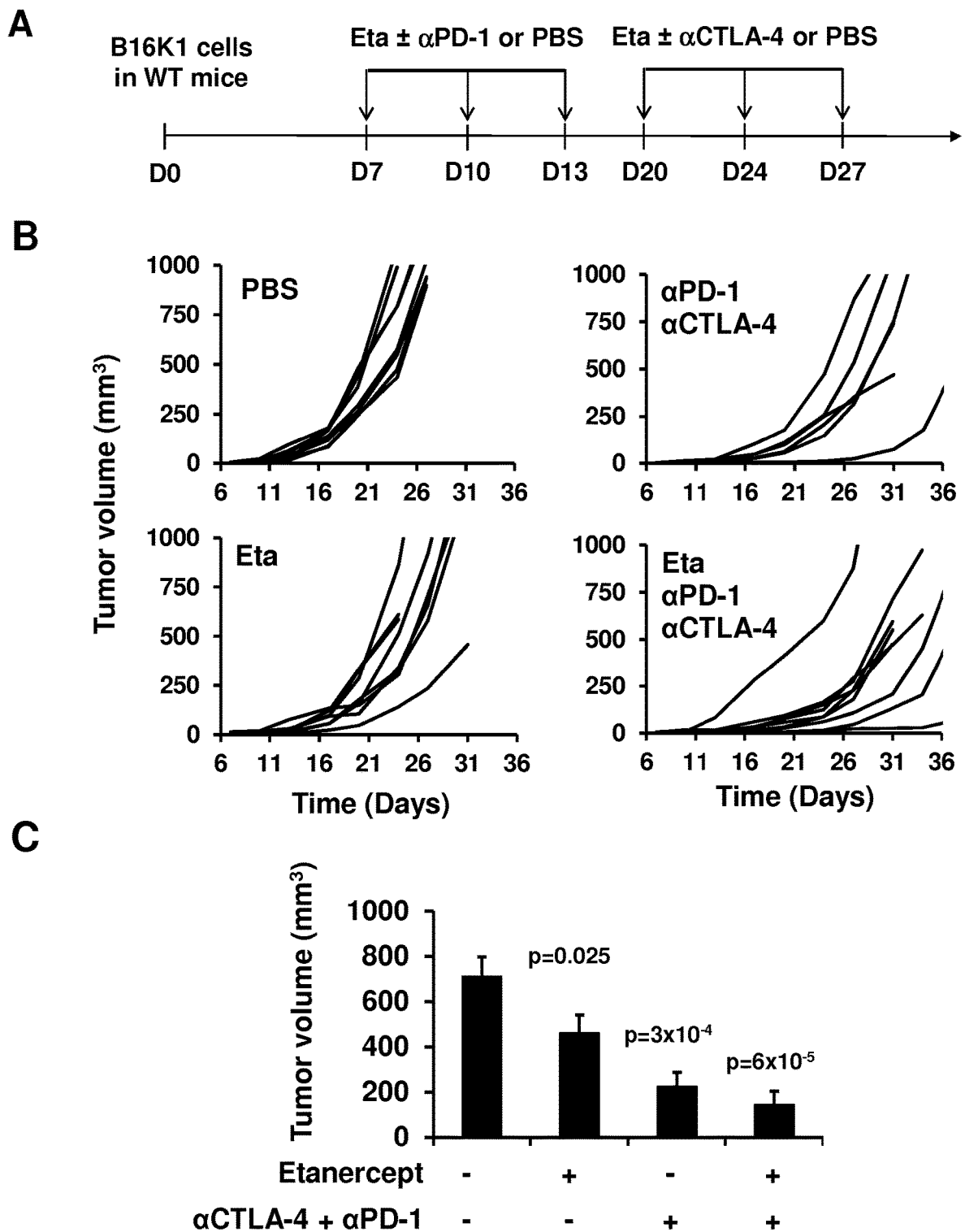

FIG. 5: Etanercept injection in combination with anti-CTLA-4 and anti-PD-1 in wild-type mice with established melanoma. C57BL/6 wild-type mice were intradermally and bilaterally grafted with $3\times10^5$ B16K1 melanoma cells before intraperitoneal injection of vehicle (PBS) or Etanercept (Eta, 3 mg/Kg) with or without the combination of anti-PD-1 (αPD-1, 5 mg/Kg) and anti-CTLA-4 (αCTLA-4, 5 mg/Kg for the first injection and then 2.5 mg/Kg) antibodies at the indicated days (n=5 mice per group). A, Scheme representing the experimental protocol. B and C, Tumor volumes were determined with a calliper at the indicated days. Individual curves are depicted for each tumor (B). Bars represent mean values determined at day 24. P values are calculated by using the Student's t-test for each condition as compared to the vehicle (PBS)-injected mice (C).

Figure 6:
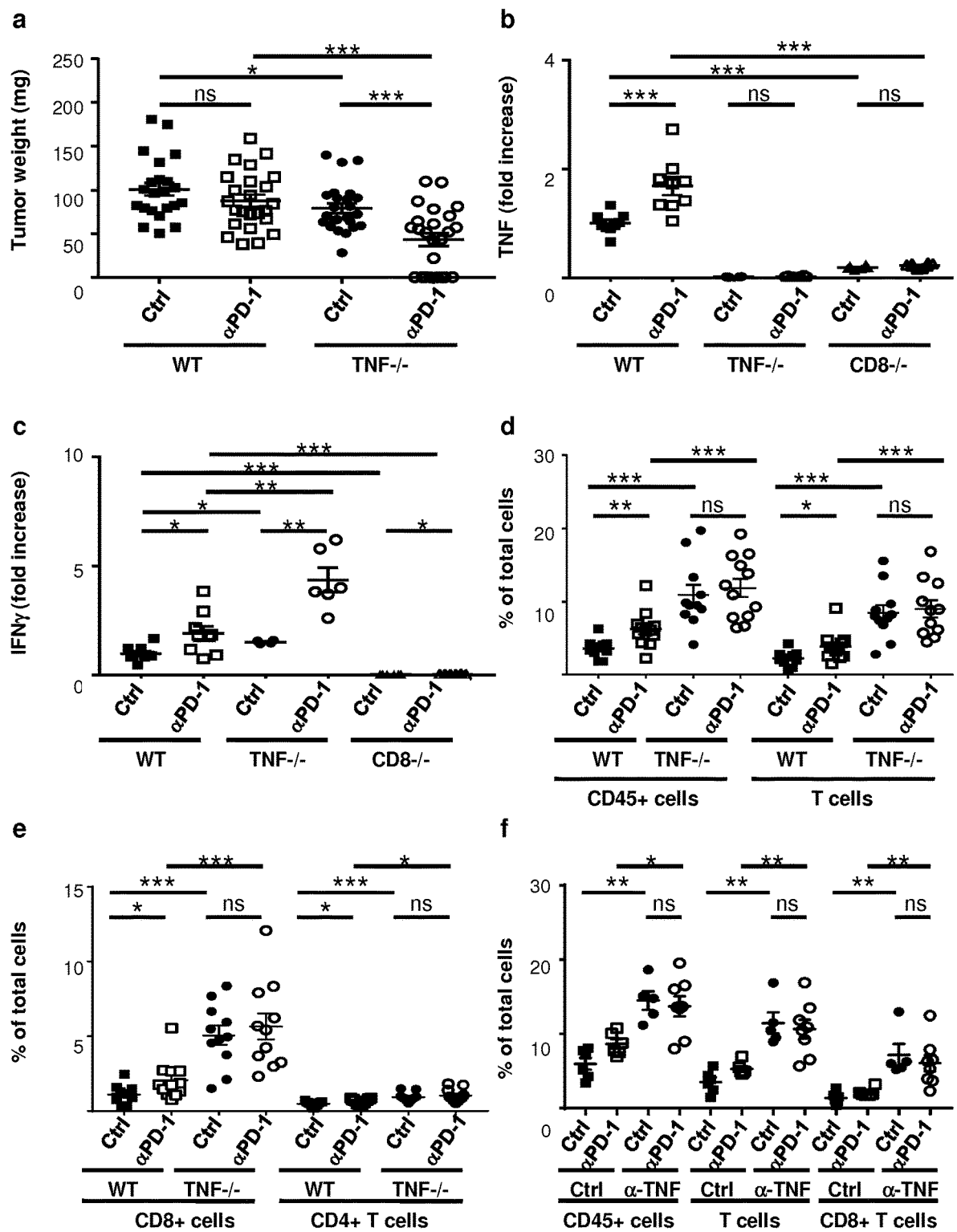

FIG. 6: Immune cell infiltration of tumors from anti-PD-1 treated wild-type and TNF-deficient mice with established melanoma. a-e, C57BL/6 wild-type (WT) and TNF-deficient mice (TNF−/−) were intradermally and bilaterally grafted with $1\times10^6$ B16K1 melanoma cells prior to intraperitoneal injection of anti-PD-1 antibodies (αPD-1, 10 mg/Kg) or vehicle (PBS; Ctrl) at day 7. a, At day 10, mice were sacrificed and tumors were weighed. Data are means±sem of at least 22 tumors per group. b and c, TNF and IFN transcript levels were quantified by RT-qPCR using total mRNA purified from tumors. Data are means±sem of at least 4 tumors per group. d and e, Tumors were dissociated and the TIL content analysis was analysed by using flow cytometry. The proportion of total CD45+, Thy1+, CD4+ and CD8+ TILs among total cells was determined. Data are means±sem of at least 11 tumors per group. f, C57BL/6 wild-type mice were intradermally and bilaterally grafted with $1\times10^6$ B16K1 melanoma cells prior to intraperitoneal injection of anti-TNF (αTNF, 10 mg/Kg) or vehicle (Ctrl) at days 5 and 7 with anti-PD-1 antibodies (αPD-1, 10 mg/Kg) or vehicle (PBS) at day 7. At day 10, TILs were analysed by flow cytometry. Data are means±sem of at least 5 tumors per group. (*p<0.05; p<0.01; *p<0.001).

Figure 7:
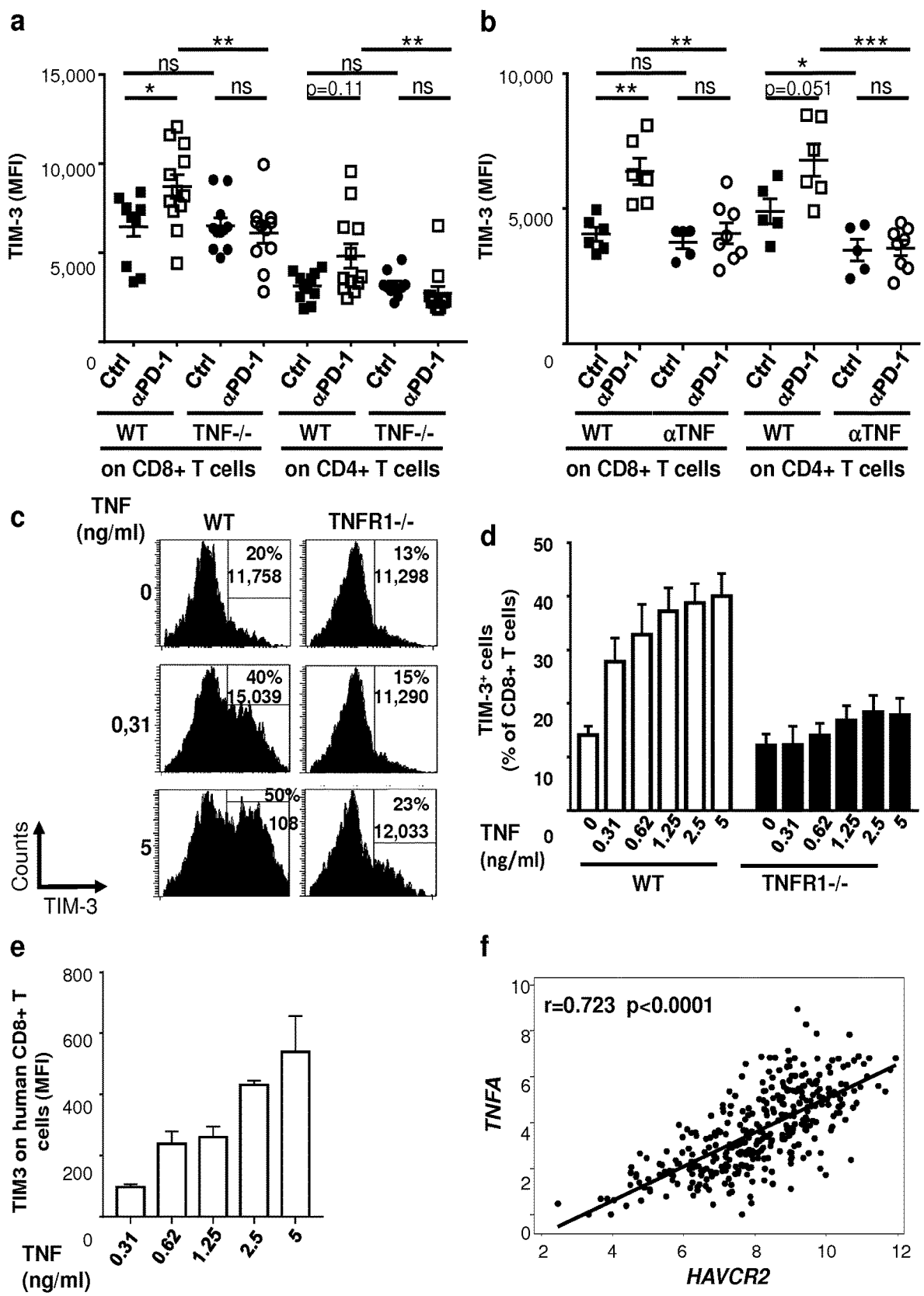

FIG. 7: TNF expression is positively correlated with TIM-3 expression in human melanoma samples. Correlation analysis between the expression of HAVCR2 (encoding TIM-3) expression and TNFA (encoding TNF) in melanoma samples from metastatic melanoma patients from the TCGA cohort (n=342). (p<0.0001).

Figure 8:
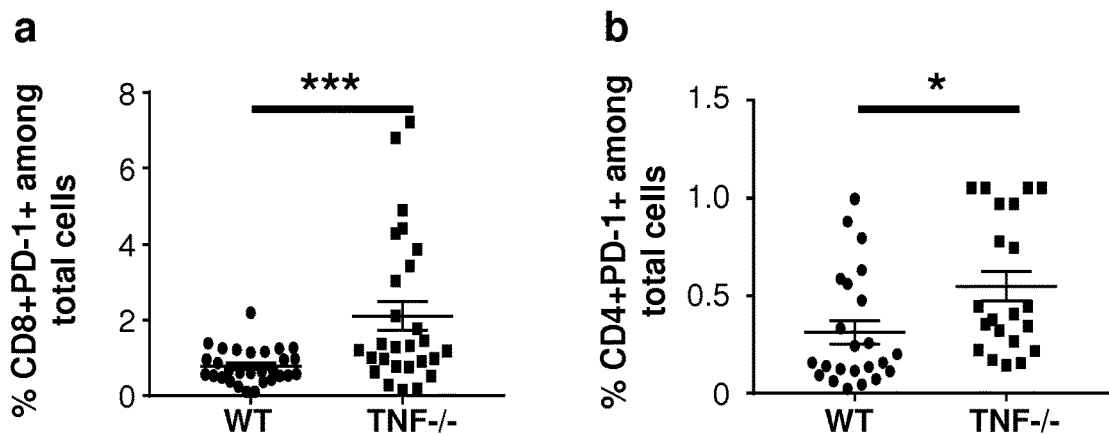

FIG. 8: TNF deficiency enhances TIL PD-1+ content. C57BL/6 wild-type (WT) and TNF-deficient mice were intradermally and bilaterally grafted with $1\times10^6$ B16K1 melanoma cells. At day 10, tumors were collected and dissociated and tumor content analysis was performed by using flow cytometry. The proportion of CD8+ and CD4+ TILs expressing PD-1 among total cells was determined. Data are means±sem of at least 21 tumors per group (*p<0.05; ***p<0.001).

Figure 9:
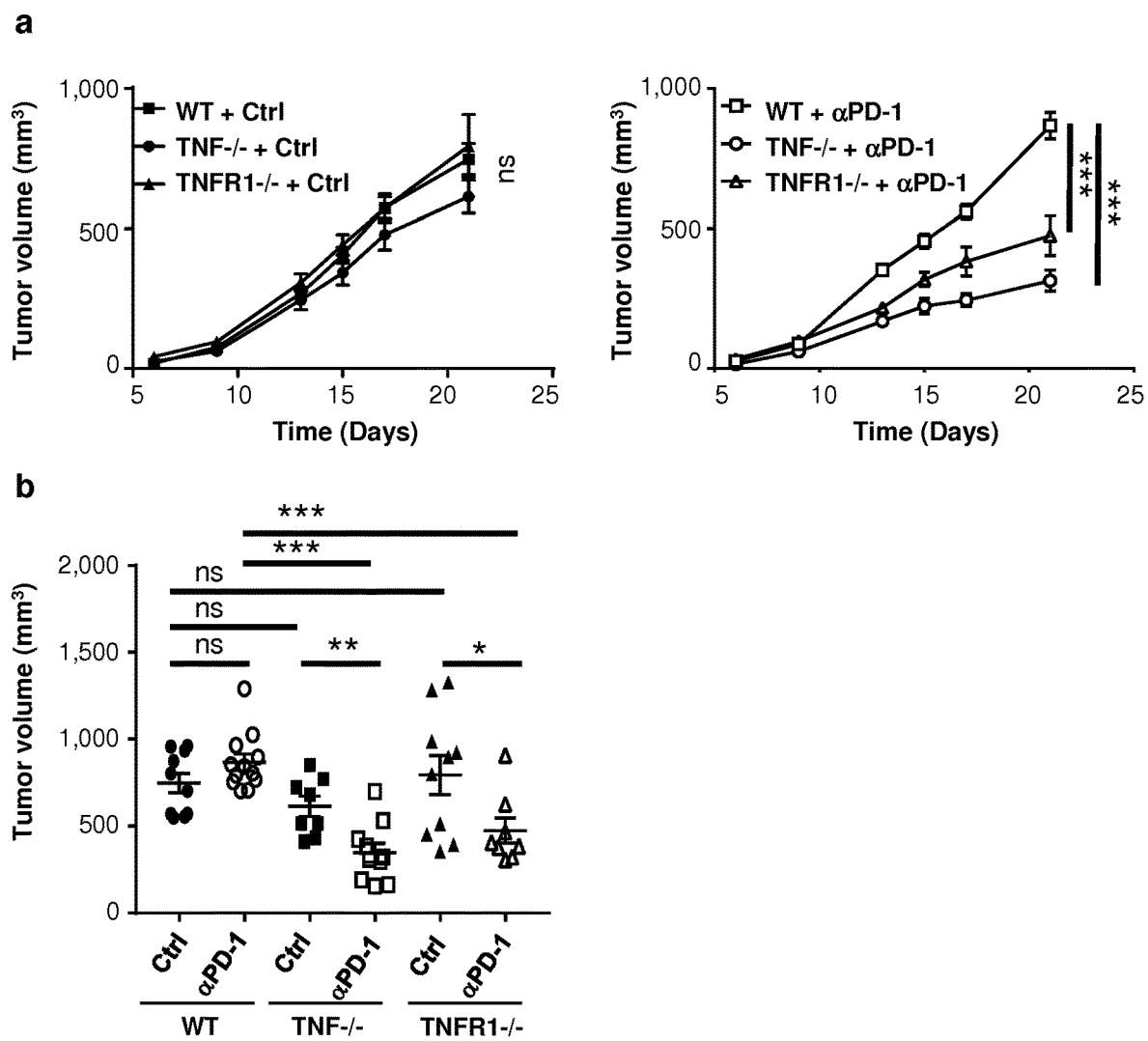

FIG. 9: Deficiency in TNF or TNFR1 potentiates anti-PD-1 therapy in established Lewis lung carcinoma (LLC). C57BL/6 wild-type (WT), TNF-deficient and TNFR1-deficient mice were intradermally and bilaterally grafted with $4\times10^5$ LLC cells before intraperitoneal injection of anti-PD-1 antibodies (αPD-1, 10 mg/Kg) or a relevant isotype control (Ctrl, 10 mg/Kg) at days 6, 9 and 13. a, Tumor volumes were determined with a calliper at the indicated days. Data are mean±sem of at least 4 mice per group. b, Values determined at day 20 for individual tumors are depicted. Bars represent mean values±sem (*p<0.05; p<0.01; *p<0.001).

Figure 10:
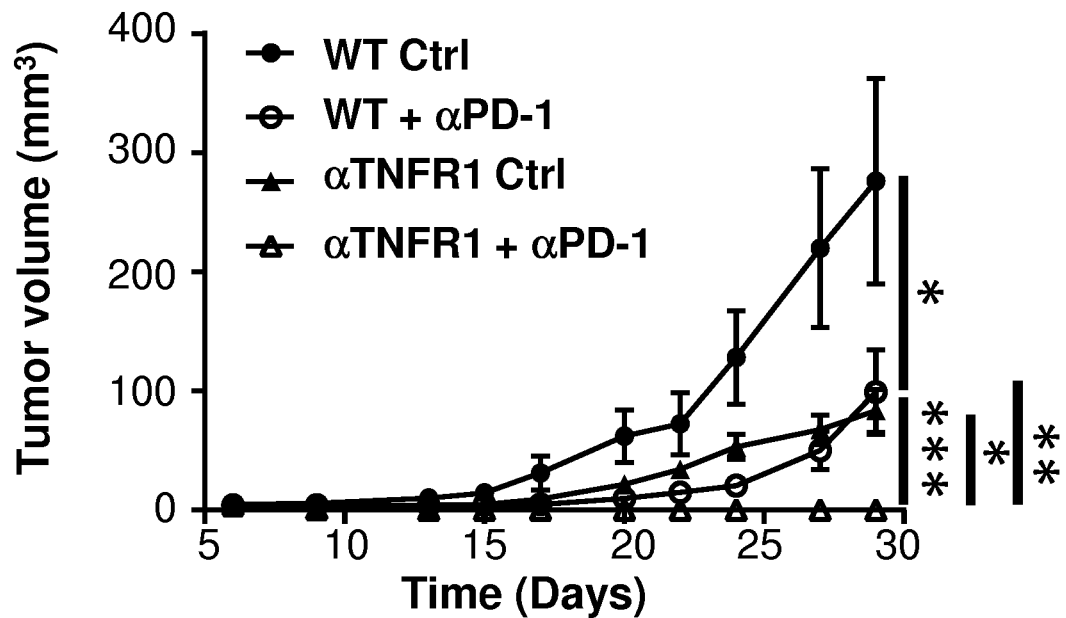

FIG. 10: anti-TNFR1 synergise with anti-PD-1 in experimental melanoma. C57BL/6 wild-type mice were intradermally and bilaterally grafted with $3\times10^5$ B16K1 melanoma cells. Mice received two injections of anti-TNF-R1 and anti-PD-1 antibody at day 6 and 9 (10 mg/Kg) alone or in combination. Alternatively, mice were injected with isotype control (Ctrl). Tumor volumes were determined with a calliper at the indicated days. Data are mean±sem of at least 4 mice per group. Bars represent mean values±sem. (*p<0.05; p<0.01; *p<0.001).

Figure 11:
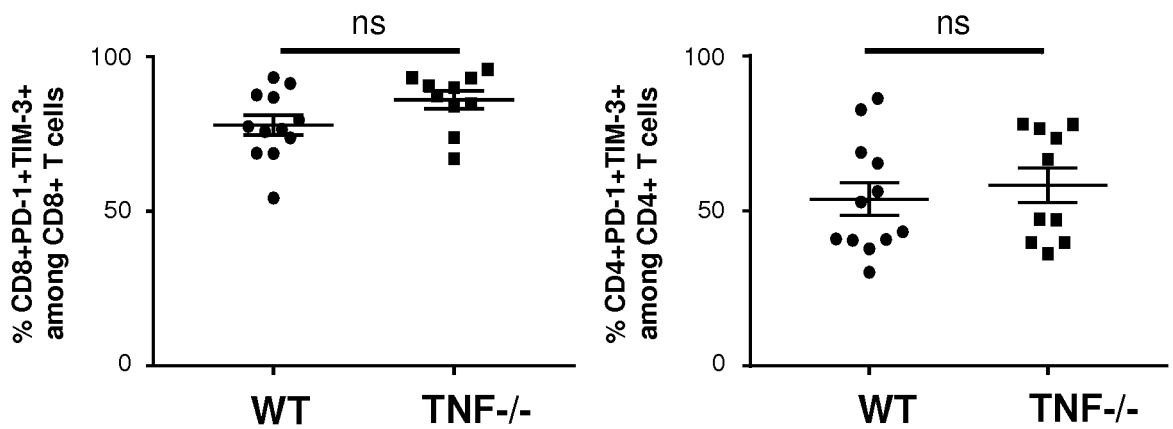

FIG. 11: Analysis of TIM-3 and PD-1 expression on TILs. C57BL/6 wild-type (WT) and TNF-deficient mice were intradermally and bilaterally grafted with $1\times10^6$ B16K1 melanoma cells. At day 10, tumors were collected and dissociated and tumor content analysis was performed by using flow cytometry. The proportion of CD8+ and CD4+ T cells co-expressing PD-1 and TIM-3 was determined among CD8+ and CD4+ T cells, respectively. Data are means±sem of at least 10 tumors per group (*p<0.05; p<0.01; *p<0.001).

Figure 12:
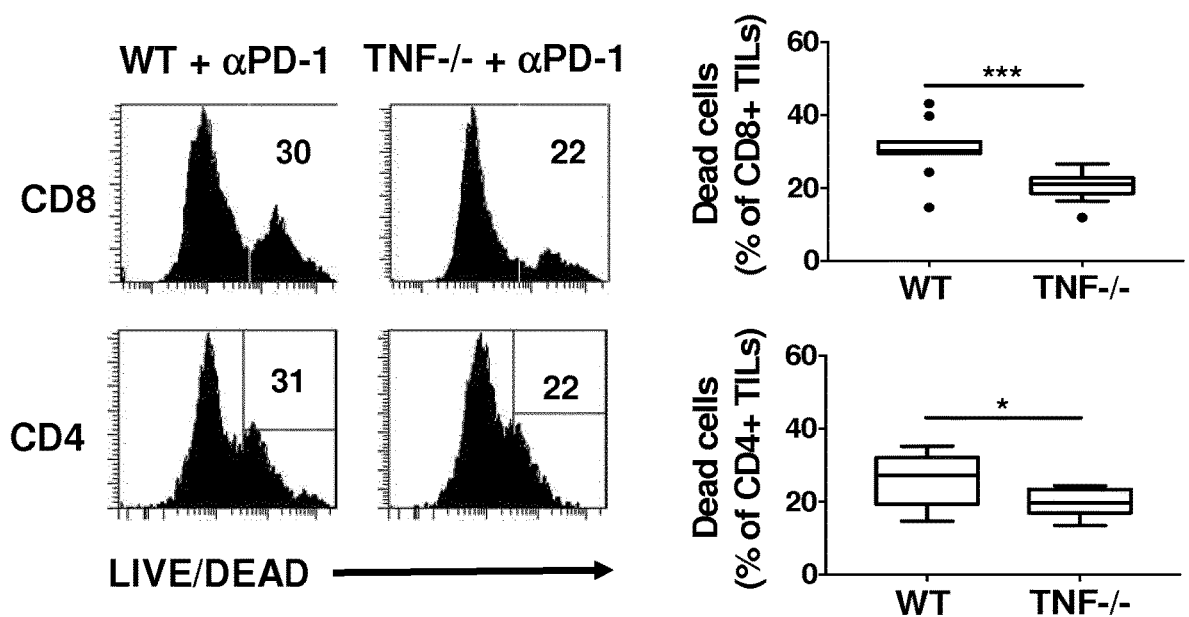

FIG. 12: TNF triggers cell death in CD4+ and CD8+ TIL upon anti-PD-1 therapy. C57BL/6 wild-type (WT) and TNF-deficient mice (TNF−/−) were intradermally and bilaterally grafted with $1\times10^6$ B16K1 melanoma cells prior to intraperitoneal injection of anti-PD-1 antibodies (αPD-1, 10 mg/Kg) at day 7. At day 10, the proportion of dead CD8+ and CD4+ TILs was analysed by flow cytometry. Values measured in 12 tumors per group from two independent experiments are represented as Tukey boxes (Student's t-test: *p<0.05; ***p<0.001).

Figure 13:
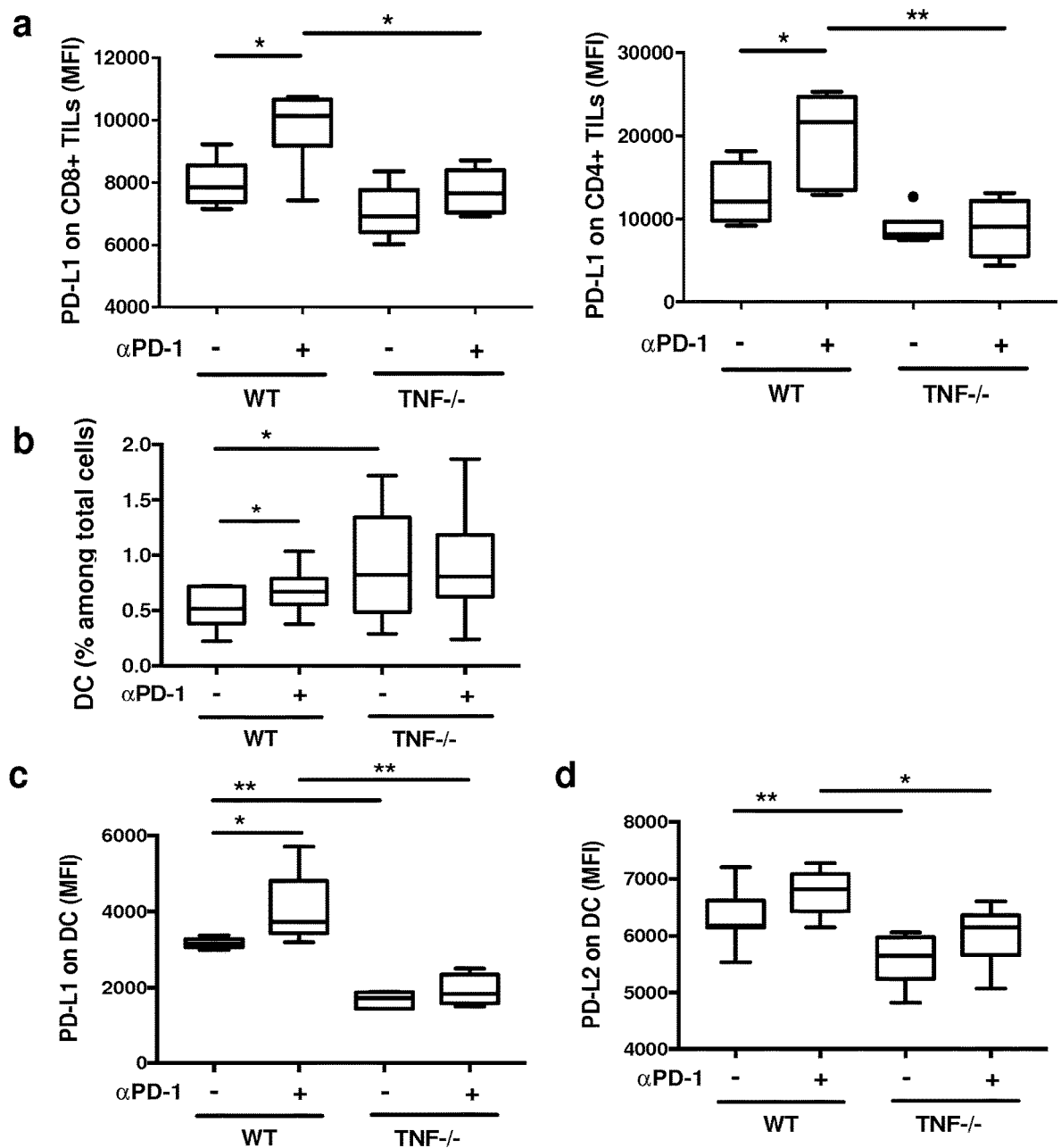

FIG. 13: TNF induces PD-L1 and/or PD-L2 expression on TILs and DC. WT and TNF-deficient (TNF−/−) mice were injected as described in the legend to FIG. 13. TILs were analysed by flow cytometry on tumors developed at day 10. a, Mean of fluorescence intensity (MFI) for the PD-L1 staining on CD8+ TILs (left panel) and CD4+ TILs (right panel). b, Percentage of tumor DC among total cells. c-d, Mean of fluorescence intensity (MFI) of PD-L1 (c) or PD-L2 (d) staining on DC. a-d, Values measured in at least 6 tumors per group from one (out of two) representative experiment are represented as Tukey boxes (Mann-Whitney U test: *p<0.05; **p<0.01).

Figure 14:
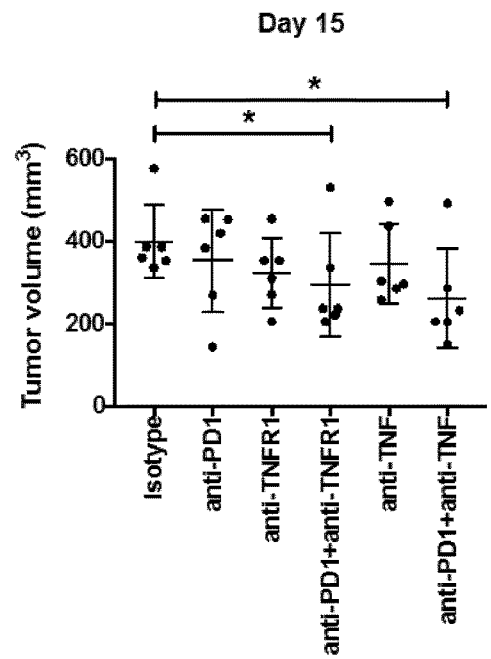

FIG. 14: anti-TNF and anti-TNFR1 antibodies overcome the resistance to anti-PD-1 therapy in experimental breast carcinoma. $1\times10^5$ 4T1 breast carcinoma cells were orthotopically injected into the mammary fat pad of WT Balb/c mice. Mice were next injected with isotype control, anti-TNF, anti-TNFR1, anti-PD-1 (10 mg/Kg of each antibody) or the combination of anti-PD-1 and anti-TNF or the combination of anti-PD-1 and anti-TNFR1. A Mann-Whitney U test was used and differences were statistically significant (*p<0.05) as compared to the isotype control group. Data are mean values±s.e.m. of 6 mice per group from one experiment.

Figure 15:
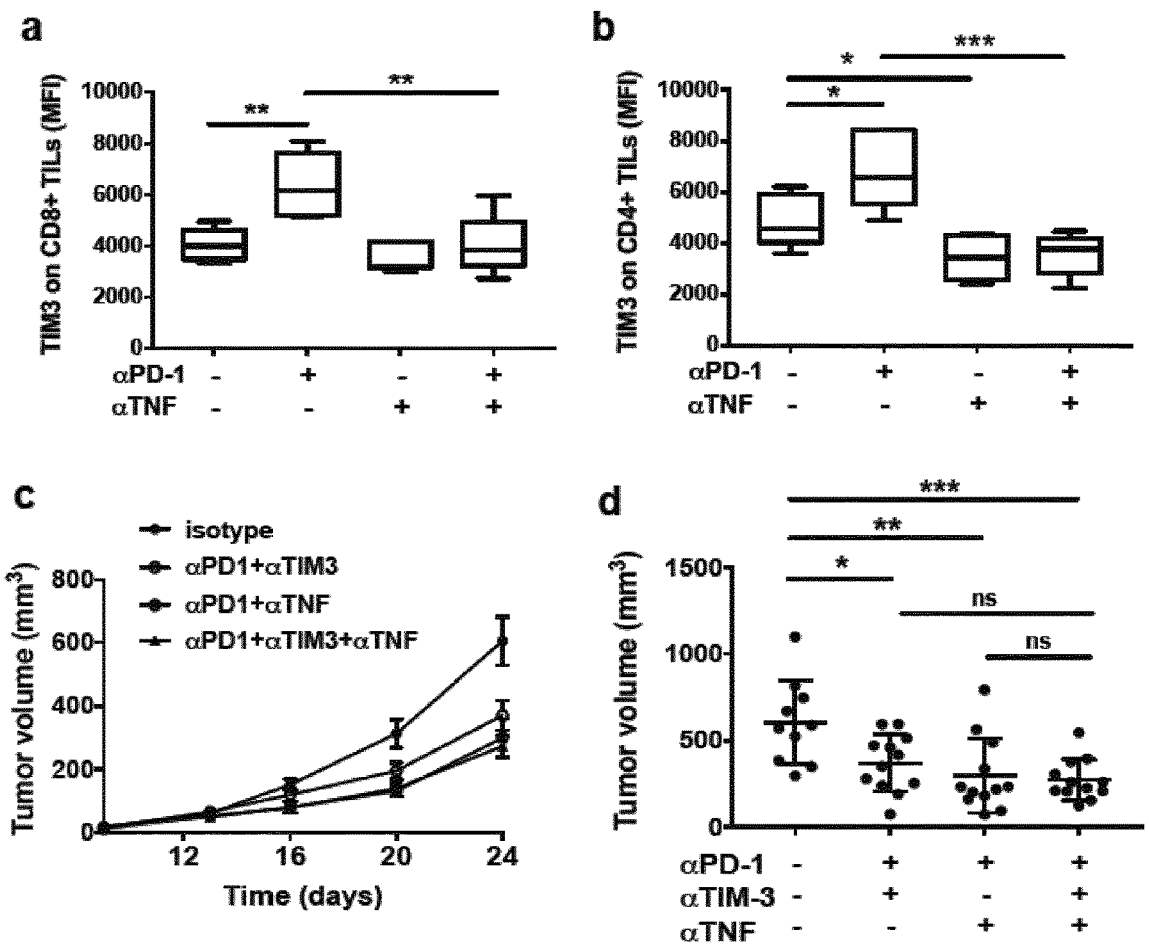

FIG. 15: TNF blockade prevents TIM-3 up-regulation on TILs in response to anti-PD-1. a and b, TIM-3 expression level on CD8+ TILs (a) and CD4+ TILs (b) was determined by flow cytometry on tumors from WT mice at day 10 after B16K1 graft following injection of vehicle (PBS), anti-PD-1 (αPD-1), anti-TNF (αTNF) or a combination of both. Mean of fluorescence intensity (MFI) on CD8+(b) and CD4+ TILs (c) measured in at least 5 tumors per group from one experiment are represented as Tukey boxes. c and d, C57BL/6 WT mice were intradermally and bilaterally grafted with 1×10⁶ B16K1 melanoma cells prior to injection with isotype control or anti-PD-1 combined with anti-TNF and/or anti-TIM-3 (10 mg/Kg of each antibody) at days 13, 17, and 20 (n=5-6 mice per group). Data are from one experiment. Tumor volumes were determined with a calliper. Data are means±s.e.m (c). Tumor volumes determined at day 24 for individual tumors are depicted. Bars represent mean values±sem (d). (a-d: Mann-Whitney U test: ns: not significant; *$p<0.05$; $p<0.01$; *$p<0.001$).

EXAMPLES

Example 1

Material & Methods:

Reagents and antibodies: Anti-PD-1 (clone: RMP1-14), anti-CTLA-4 (clone: 9H10), anti-TNF (clone: XT3.11), isotype control antibodies were purchased from BioXcell and anti-TNFR1 (clone: 55R-170) from Ozyme. Additional antibodies used in this study were anti-mouse CD45 (BD Biosciences, BUV395), anti-mouse Thy1 (Biolegend®, APC-Cy7), anti-mouse CD8 (BD Biosciences, BV605), anti-mouse CD4 (eBioscience, FITC), anti-TIM3 (Biolegend®, PE-Cy7), anti-CD11c (eBioscience, PE-Cy7), anti-CD3 (Biolegend®, FITC), anti-CD19 (Biolegend®, FITC), anti-NK1.1 (BD Biosciences, FITC), anti-PD-L1 (BD Biosciences, PE) and anti-PD-L2 (BD Biosciences, APC). Etanercept was provided by Dr. Astudillo (CHU, Toulouse, France).

Cell Lines:

B16K1 is a genetically modified C57BL/6 mouse melanoma cell line obtained from B16F10 cells, and stably expressing the MHC-I molecule H-2Kb, stimulating CD8 T cell-dependent immune responses[1,2]. Cells were cultured in DMEM medium containing 10% heat-inactivated fetal calf serum (FCS). Medium was changed every 2-3 days. Lewis lung carcinoma cells (LLC) and 4T1 breast cancer cells were from ATCC. Cells were cultured for a limited number of passages in DMEM medium containing 10% FCS and tested for the absence of *mycoplasma* contamination by PCR.

Mice:

TNF-deficient (#5540) and TNFR1-deficient (#2818) C57BL/6 mice were purchased from Jackson laboratories. WT C57BL/6 mice were from Janvier. Mice were housed in temperature-controlled rooms in the specific pathogen-free animal facility (Anexplo platform, Toulouse, France), kept on a 12-h light/dark cycle, and had unrestricted access to food and water. All animal studies were conducted according to national and international policies and were approved by the local committee for animal experimentation.

In Vivo Tumorigenesis:

3×10⁵ B16K1 or 4×10⁵ LLC cells were intra-dermally and bilaterally injected in wild-type, TNF-deficient and TNFR1-deficient mice. Anti-PD-1 (10 mg/Kg) or isotype control (10 mg/Kg) was next intraperitoneally injected at day 6, 10 and 13 after B16K1 graft. Anti-TNF[3] (10 mg/Kg) was inoculated at day 6, 10, 13 and 16 and anti-TNFR1[3] (10 mg/Kg) at day 6 and 10. Alternatively, mice were injected with relevant isotype control antibodies (10 mg/Kg). Alternatively, we have established a protocol combining an anti-TNF (Etanercept) with the αPD-1 and αCTLA-4 blocking antibodies in wild-type mice. 3×10⁵ B16K1 cells were intra-dermally and bilaterally injected in wild-type mice (n=5 mice per condition). The control and the Etanercept-treated groups were performed by intraperitoneally injecting 7 days post B16K1 graft and twice a week throughout the experiment, vehicle (PBS) and Etanercept (3 mg/Kg), respectively. Mice were treated with αPD-1 and αCTLA-4 intraperitoneally at day 7, 13 and 17 with the αPD-1 (5 mg/Kg) and at day 20, 24 and 27 with the αCTLA-4 (5 mg/Kg for the first injection and then 2.5 mg/Kg). Tumor volume was calculated using a calliper at the indicated days. Tumor volume was calculated using a caliper at the indicated days with the formula: Tumor volume=0.52×length×width².

Overall Survival:

The overall survival was estimated taking into account the time of natural death of animals or, alternatively, the time of sacrifice when tumors reached 10% of body weight (i.e., total tumor volume of 2,000 mm³), according to national and international policies.

Analysis of tumor transcripts: 10⁶ B16K1 cells were intra-dermally injected in WT, TNF-deficient and CD8-deficient mice. Anti-PD-1 (10 mg/Kg) or vehicle (PBS) was next intraperitoneally injected at day 7. At day 10, mice were sacrificed and tumors were collected and dissociated by using tissue homogenizer (Precellys Evolution, Bertin Technologies SAS) at 8,000 rpm for 2 cycles of 30 s in vials containing ceramic balls. RNA was purified using the RNeasy Midi Kit (Qiagen). cDNA from total RNA was prepared with SuperScript™ II Reverse Transcriptase (Thermofisher) by using 1 µg of RNA from each sample. qPCR was performed using SYBR Green Master Mix (Takara) and primers for transcripts encoding murine β-actin, HPRT, TNFα and IFNγ (Qiagen).

Analysis of TIM-3 induction on purified lymphocytes: Murine naive CD8+ T cells were purified from spleen of naive WT or TNFR1-deficient mice using a mouse naive CD8+ T cell purification kit (Miltenyi Biotec). Human naive CD8+ T cells were isolated from whole blood of healthy donors using a human naive CD8+ T cell purification kit (Miltenyi Biotec). Murine and human T cells were activated with anti-CD3 and antiCD28-coated beads (Life Technologies) and anti-CD3, anti-CD28 and anti-CD2 coated beads (Miltenyi), respectively, in the presence of IL-2 (Invitrogen; 200 U/mL). Activated CD8+ T cells were incubated for 48 hours in the presence of recombinant either murine or human TNF (Peprotech) and TIM-3 expression was then evaluated by flow cytometry.

4T1 Breast Cancer Cell Growth in Mice.

1×10⁵ 4T1 cells were orthotopically injected into the mammary fat pad of Balb/c mice. Mice were next injected with isotype control, anti-PD-1, anti-TNF or the combination of anti-PD-1 and anti-TNF (10 mg/Kg of each antibody) at day 6, 9 and 13. Tumor volume was calculated using a caliper at the indicated days with the formula: Tumor volume=0.52×length×width².

Analysis of TNF, TIM3, PDL1/2 Expression in Human Melanoma.

TNF expression was analysed using the TCGA melanoma cohort. TCGA genomic and clinical data were downloaded from the UCSC cancer genome browser project (https://genomecancer.ucsc.edu). The analysis population consisted of 342 patients with distant metastasis for whom RNAseq and clinical data overlap. No formal sample size calculation was performed concerning TCGA analysis. All patients fulfilling inclusion and non-inclusion criteria were included in this analysis. Gene expression was measured experimentally using the Illumina HiSeq 2000 RNA Sequencing platform and log 2(x+1) transformed. Alternatively, TNF expression was analysed in melanoma biopsies from patients treated with anti-PD-1 (our analysis of data published by Chen et al., Cancer Discov 6, 827-837 (2016)). The strength of relationship between TNF and TIM-3 encoding genes was assessed using Spearman's rank correlation coefficient.

Statistical Analysis:

Statistical significance of difference between groups was evaluated by using the Graph-Pad Prism software. Briefly, we tested if the values come from a Gaussian distribution with a D'agostino-Pearson omnibus normality test. When passing the normality test, a Student's t-test was used. Otherwise, a Mann-Whitney U test was used. Differences were considered to be statistically significant when $p<0.05$ (*$p<0.05$; $p<0.01$; *$p<0.001$). For statistical significance of survival, a gehan-breslow-wilcoxon test was used.

Example 2

TNF or TNF-R1 Inhibition Improves Anti-PD-1 Therapy Against Melanoma.

We have recently demonstrated that host TNF-R1-dependent TNF signalling impairs the CD8+ T cell tumor content in mouse melanoma by triggering activated CD8+ T cell death and limiting the intra-tumor density of high endothelial venules, which are blood vessels involved in lymphocyte tissue infiltration. Consequently, the injection of Etanercept, which efficiently neutralizes mouse TNF, significantly reduces MHC-I$^{high}$ melanoma (B16K1) growth in immunocompetent but not immunodeficient (i.e., Nude, IFNγ and CD8 KO) mice. Emerging immunotherapy, including αPD-1 blocking antibodies have proved clinical efficacy for the treatment of patients affected with metastatic melanoma. Herein, we have evaluated the effect of TNF or TNF-R1 blockade strategy on melanoma development in combination with αPD-1 immunotherapy. We have selected B16K1 mouse melanoma cell lines, which express MHC-I at high levels, and therefore represent an appropriate model to study the CD8+ T cell-dependent immune response. B16K1 were orthotopically injected in both wild-type and TNF-deficient mice and mice were next intraperitoneally injected with αPD-1 or an appropriated isotype control as indicated in FIG. 1a. In agreement with our previous observations, the B16K1 tumor growth was significantly reduced in TNF KO mice as compared to their wild-type counterparts (FIGS. 1b and c). Moreover, there was a significant delay of the death of TNF-KO mice as compared to control mice. In wild-type mice, the anti-PD-1 blocking antibody injection significantly delayed the B16K1 tumor growth and this phenomenon was greatly enhanced in TNF-deficient animals (FIGS. 1b and 1c). Whereas anti-PD1 injection led to the total regression of 8 tumors out of 22 in WT mice, it triggered 20 tumor rejection out of 22 in TNF KO mice. In addition, upon anti-PD-1 injection, survival rate was dramatically improved in TNF-deficient mice (9 out of 11 mice) as compared to wild-type mice (0 out of 11 mice) (FIG. 1d). Two months after the first B16K1 cell injection, B16K1 cells were re-injected in the survival TNF KO mice. None of the mice developed tumors in contrast to wild-type control mice, which have not been experienced with B16K1 cells before (FIG. 1d). The latter observation indicates that all the survival TNF KO mice were totally vaccinated towards B16K1 cells. Thus, TNF signalling is unlikely required for the establishment of an efficient memory CD8+ T cell response against melanoma We have next evaluated the consequences of TNF-R1 deficiency on the therapeutic activity of anti-PD-1 blocking antibodies. B16K1 cells were orthotopically injected in WT and TNF-R1-deficient mice and mice were next intraperitoneally injected with αPD-1 or isotype control as indicated in FIG. 2a. In agreement with our previous observations, the B16K1 tumor growth was significantly reduced in TNF-R1 KO mice as compared to their wild-type counterparts (FIGS. 2b and c). Moreover, there was a significant delay of the death of TNF-R1 KO mice as compared to control mice. Whereas anti-PD-1 significantly delayed tumor growth in wild-type mice (FIGS. 2b and c) and death (FIG. 2d), most of the tumors relapsed and all mice died within 60 days post-tumor cell injection. In sharp contrast, all tumors totally regressed in TNF-R1-deficient mice injected with anti-PD-1 antibodies (FIG. 2b, right panel). From day 26, tumors could be detected in none of the TNF-R1 KO animals treated with anti-PD-1 antibodies (FIG. 2c). Moreover, all mice survived in sharp contrast to the isotype-injected group in which all mice died within 40 days post B16K1 cell injection (FIG. 2d). Two months after the first B16K1 cell injection, B16K1 cells were re-injected in the survival TNF-R1 KO mice and none of the mice developed tumors (FIG. 2). The latter observation indicates that, like TNF KO mice injected with anti-PD-1, all the survival TNF-R1 KO mice were totally vaccinated towards B16K1 cells.

Collectively, our data indicate that TNF-R1-dependent TNF signalling is not required for the anti-melanoma immune response triggered by anti-PD-1 antibodies but rather inhibits the therapeutic benefit of PD-1 blockade in melanoma. Inhibiting TNF or TNF-R1 may therefore facilitates the anti-PD-1 efficacy to fight against melanoma.

Example 3

Anti-TNF Injection in Combination with Anti-PD-1 Blocking Antibodies in Wild-Type Mice with Established Melanoma.

Results from clinical trials indicate that therapy with anti-PD-1 blocking antibodies is a promising strategy in metastatic melanoma. However, some patients do not benefit from the treatment and a proportion of them exhibit serious immune-related adverse effects, including autoimmune and inflammatory reactions. Taking into account (i) our above observations indicating that TNF/TNF-R1 inhibition improves the anti-PD-1 therapeutic efficacy in mouse melanoma, (ii) our recent findings illustrating that anti-TNF injection enhances the CD8+ T cell-dependent immune response against melanoma and (iii) the efficacy of some anti-TNF blocking molecules to inhibit autoimmune and inflammatory syndromes in the Clinic, we have designed a protocol to evaluate the anti-TNF combination with anti-PD-1 blocking antibodies in mouse melanoma (FIG. 3A). As compared to the isotype injected control mice, anti-TNF alone slightly inhibited B16K1 melanoma growth (FIGS. 3B and C). The injection of anti-PD-1 blocking antibodies alone was accompanied by a greater delay in tumor growth with a total regression of 7 tumors out of 24 in control mice. Interestingly, the combination of anti-PD-1 with anti-TNF increased this phenomenon with a total regression of 18 tumors out of 24 (FIGS. 3B and C). Moreover, anti-PD-1 injection combined with anti-TNF led to the survival of 9 mice out of 12 as compared to 2 mice out of 12 in the group injected with anti-PD-1 alone.

Collectively, our data indicate that anti-TNF does not compromise but rather enhances, at least to some extent, the therapeutic effect of the anti-PD-1 in melanoma.

Example 4

Tumor Infiltration of Immune Cells in Melanoma Developed in WT and TNF-Deficient Mice Injected with Anti-PD-1 Blocking Antibody Because we have previously shown that the host TNF-R1-dependent TNF signalling impairs the CD8+ T cell tumor content in mouse melanoma, we next investigated the effect of anti-PD-1 on TILs in WT and TNF-deficient mice. To this end, mice were orthotopically injected with 1 million of B16K1 cells. At day 7, mice were injected with anti-PD-1 antibody or vehicle and sacrificed at day 10 (FIG. 4A). Under those conditions, B16K1 tumor weights were significantly reduced in TNF-deficient mice as compared to WT mice and this phenomenon was amplified upon anti-PD-1 injection (FIG. 4B). Analysis of leukocyte tumor content by flow cytometry indicated that anti-PD-1 injection in WT mice induced a small, yet significant, increase of CD45+ cells as well as CD8+ and CD4+T lymphocytes compared to control WT mice (FIG. 4C). In good agreement with our published data, CD45+ cells as well as CD8+ and CD4+ TILs were dramatically increased in TNF-deficient mice, this phenomenon being not further enhanced upon anti-PD-1 injection (FIG. 4C). Taking into account the major role of TIM-3 in the immune escape mechanisms associated with resistance to anti-PD-1 both in mice and patients, we then evaluated TIM-3 expression on TILs. Of note, approximately 70% of CD8+ and CD4+ TILs co-expressed PD-1 and TIM-3, irrespectively of the TNF status (FIG. 11). The mean fluorescence intensity of TIM-3 staining on CD8+ and CD4+ T cells was increased following anti-PD-1 injection in WT mice (FIG. 4D). In sharp contrast, this phenomenon was totally abolished in TNF KO mice (FIG. 4D), suggesting that anti-PD1-triggered TIM-3 expression occurred in a TNF-dependent manner. To evaluate whether TNF is a potent inducer of TIM-3 expression, we incubated purified and activated murine CD8+ T cells with exogenous and sub-toxic dose of murine TNF. TNF induced an increase of the percentage of TIM-3+ cells and the mean fluorescence intensity of TIM-3 staining (FIG. 4E).

Altogether, our data show that TNF deficiency not only enhances CD4+ and CD8+ TIL content but also prevents the up-regulation of TIM-3 triggered by anti-PD-1 in melanoma.

Example 5

Etanercept Injection in Combination with Anti-CTLA-4 and Anti-PD-1 Blocking Antibodies in Wild-Type Mice with Established Melanoma.

Recent clinical trials indicate that combination therapy associating anti-PD-1 and anti-CTLA-4 blocking antibodies is a promising strategy in metastatic melanoma. However, a great proportion of patients exhibit serious immune-related adverse effects, including autoimmune and inflammatory reactions, which can be cured with anti-TNF. We have designed a protocol to evaluate the Etanercept combination with anti-PD-1 and anti-CTLA-4 blocking antibodies in mouse melanoma (FIG. 5A). As compared to the vehicle (PBS)-injected control mice, Etanercept alone significantly inhibited B16K1 melanoma growth (FIGS. 5B and C). The injection of anti-PD-1 and anti-CTLA-4 blocking antibodies was accompanied by a greater delay in tumor growth, this phenomenon being more pronounced by Etanercept injection (FIGS. 5B and C).

Collectively, our data indicate that Etanercept does not compromise but rather enhances, at least to some extent, the therapeutic effect of the anti-PD-1 and anti-CTLA-4 combination in melanoma.

Example 6

Since pre-existing CD8+ TILs that are negatively regulated by PD-1 pathway are predictive of the response to anti-PD-1 in melanoma patients[29], we initially evaluated the expression of PD-1 and its ligands (PD-L1 and PD-L2) in B16K1 tumors from wild-type (WT) and TNF-deficient mice. The proportion of CD8+PD-1+ TILs (FIG. 8a) and CD4+PD-1+ TILs (FIG. 8b) was increased in melanoma tumors from TNF-deficient mice. Thus, TNF deficiency enhances the tumor content of key effector lymphocytes expressing PD-1.

We next investigated the effect of TNF deficiency or blockade in combination with αPD-1 on melanoma development. To this end, WT and TNF-deficient mice were injected with melanoma cells and when tumors became detectable on day 6, mice received the first out of three injections of anti-PD-1 blocking antibody or isotype control. In agreement with our previous reports[11], B16K1 tumor growth (FIGS. 1a and 1b) and animal death (FIG. 1c) were significantly delayed in TNF-deficient mice as compared to their WT counterparts. In WT mice, the anti-PD-1 blocking antibody injection significantly retarded the B16K1 tumor growth. However, most of the tumors relapsed and all mice died within 60 days post-tumor cell injection (FIGS. 1a, 1b and 1c). Interestingly, in TNF-deficient mice, anti-PD-1 therapy induced the tumor rejection of 90% of tumors (FIGS. 1a and 1b). Moreover, more than 80% of TNF-deficient mice survived up to 120 days (FIG. 1c). Similar data were obtained in TNFR1-deficient mice, which potently rejected B16K1 melanoma cells upon anti-PD-1 therapy (FIGS. 2a and 2b). Two months after the first B16K1 melanoma cell inoculation, B16K1 melanoma cell re-injection in the surviving TNF- and TNFR1-deficient mice did not compromise overall survival, demonstrating that they were totally vaccinated towards B16K1 melanoma cells (FIG. 1c and FIG. 2c).

To extend our observations to another cancer cell model, we then tested the effect of anti-PD1 blocking antibody in WT, TNF- and TNFR1-deficient mice injected with Lewis Lung Carcinoma cells (LLC) (FIG. 9). Neither TNF nor TNFR1 deficiency impaired LLC growth (FIG. 9a). Moreover, in WT mice, anti-PD-1 had no effect on tumor growth indicating that LLC were fully resistant to this therapy under our experimental conditions (FIGS. 9a and 9b). Of interest, TNF or TNFR1 deficiency partially overcame the resistance of LLC to anti-PD-1 (FIGS. 9a and 9b). Thus, synergism of TNF/TNFR1 deficiency and anti-PD-1 is unlikely restricted to melanoma but can be extended to other cancer types, such as lung carcinoma, which can benefit from anti-PD-1 according to phase 2 and phase 3 clinical trials[30,31]. In accordance with our preclinical data, the clinical response to anti-PD-1 is weaker in patients with lung carcinoma than in melanoma patients.

To evaluate the therapeutic relevance of the above observations, we next investigated the combination of anti-TNF and anti-PD-1 blocking antibodies in mouse melanoma (FIG. 3). As compared to control mice, anti-TNF alone slightly, yet significantly, inhibited B16K1 melanoma growth (FIG. 3). The injection of anti-PD-1 blocking antibodies alone was accompanied by a delay on tumor growth with a total regression of less than 30% of the tumors in control mice (FIG. 3). Interestingly, combining anti-PD-1 and anti-TNF led to a total regression of 75% of the tumors (FIG. 3) and to the survival of 75% of mice as compared to less than 20% in the group of mice injected with anti-PD-1 alone. Surviving mice were totally vaccinated against B16K1 (data not shown). Similar data were obtained with the combination of anti-TNFR1 and anti-PD-1 antibodies (FIG. 10). Collectively, our data indicate that TNFR1-dependent TNF signalling impairs the therapeutic benefit of PD-1 blockade.

To get insights the molecular and cellular mechanisms involved in the beneficial therapeutic effect of TNF blockade on anti-PD-1 therapy, we set up a protocol based on a single anti-PD-1 injection in WT and TNF-deficient mice seven days post-B16K1 injection. At day 10, mice were sacrificed. We observed that tumor weights were significantly reduced in TNF-deficient mice as compared to WT mice and that this phenomenon was further amplified upon anti-PD-1 injection (FIG. 6a). Interestingly, whereas one single anti-PD-1 injection failed to promote tumor rejection in WT mice, it triggered more than 30% tumor rejection in TNF-deficient mice (FIG. 6a). We next monitored the intra-tumor content of transcripts encoding TNF and IFNγ. In WT mice, anti-PD-1 injection induced an increase in the expression of both TNF and IFNγ transcripts (FIGS. 6b and c). Interestingly, in tumors from TNF-deficient mice, IFNγ transcripts were increased in control condition and further enhanced upon anti-PD-1 injection (FIG. 6c). In CD8-deficient mice, TNF and IFNγ mRNA tumor level were low under both control and anti-PD-1 conditions, demonstrating that CD8+ T cells are required for potent production of TNF and IFNγ in this melanoma model (FIGS. 6b and c).

We next investigated the effect of anti-PD-1 on TIL accumulation in WT and TNF-deficient mice injected with or without anti-PD-1. Analysis of leukocyte tumor content by flow cytometry indicated that anti-PD-1 injection in WT mice induced a small, yet significant, increase in CD45+ and T cells (FIG. 6d), including both CD8+ and, albeit to a lesser extent, CD4+ TILs (FIG. 6e). In agreement with our previous findings[11], CD45+ cells as well as CD8+ and CD4+ TILs were dramatically increased in TNF-deficient mice (FIGS. 6d and e) and in WT mice injected with anti-TNF (FIG. 60, with no further elevation upon anti-PD-1 treatment (FIGS. 6d-f). Thus, TNF blockade strongly enhances CD8+ and CD4+ TILs in mouse melanoma, a phenomenon predictive of response to anti-PD-1 in melanoma patients[29]. TIM-3, which inhibits Th1 response and triggers peripheral tolerance[32], has recently emerged as a key immune checkpoint impairing the antigen-specific CD8+ T cell response in melanoma[33] and playing a major role in the immune escape mechanisms associated with resistance of melanoma to anti-PD-1 both in mice and patients[16]. We evaluated TIM-3 expression on TILs and found more than 50% of CD8+ and CD4+ TILs co-expressing PD-1 and TIM-3, irrespectively of the TNF status (FIG. 11). The mean fluorescence intensity (MFI) of TIM-3 staining, which reflects its expression on TILs, was significantly increased on CD8+ TILs following anti-PD-1 administration in WT mice (FIG. 4D). In sharp contrast, this phenomenon was totally abolished in TNF-deficient mice (FIG. 4D), suggesting that anti-PD1-triggered TIM-3 expression occurred in a TNF-dependent manner. Importantly, anti-TNF impaired TIM-3 expression on CD4+ and CD8+ TILs in WT mice (data not shown). To evaluate whether TNF can induce TIM-3 expression, we purified and activated naive murine CD8+ T cells prior to incubation with exogenous and sub-toxic doses of murine TNF. TNF elicited an increase of both the percentage of TIM-3+CD8+ T cells and the mean fluorescence intensity of TIM-3 staining (FIG. 4E). This was abrogated in TNFR1-deficient CD8+ T cells, indicating that TNF induced TIM-3 expression in a TNFR1-dependent manner (data not shown). Of interest, TNF also stimulated the expression of TIM-3 on purified naive human CD8+ T cells (data not shown). In addition, in melanoma samples from metastatic melanoma patients from the TCGA cohort, the expression of TNFA (encoding TNF) positively and significantly correlated (r=0.723, p<0.0001) with that of HAVCR2 (encoding TIM-3) (FIG. 7), further reinforcing the close molecular link between TNF signalling and TIM-3 expression in melanoma.

Collectively, our data highlight for the first time that TNFR1-dependent TNF signalling constitutes a potent immune escape mechanism, conferring resistance to anti-PD-1, most likely by limiting CD8+ TIL content and inducing TIM-3 expression. Our study provides the proof-of-concept of combining anti-PD-1 and anti-TNF to fight melanoma and putatively other cancers such as lung carcinoma in patients.

Example 7

TNF Deficiency Reduces Cell Death of TILs Upon Anti-PD-1 Therapy.

To get insights into the molecular and cellular mechanisms involved in the beneficial effect of TNF blockade in anti-PD-1 therapy, we bilaterally grafted one million B16K1 cells in WT and TNF-deficient mice followed by a single anti-PD-1 injection seven days later.

To evaluate whether TNF deficiency impacts on TIL proliferation, we monitored Ki67 expression, a proliferation marker. The proportions of Ki67+CD8+ TIL and Ki67+ CD4+ TIL were similar in WT and TNF-deficient mice treated with anti-PD-1 (data not shown). Thus, TNF does not seem to be a major regulator of TIL proliferation under anti-PD-1 therapy. We next monitored cell death of TILs by evaluating the increase in plasma membrane permeability (LIVE/DEAD positive cells). Importantly, in anti-PD-1-treated animals, TNF deficiency significantly reduced the cell death of both CD8+ and CD4+ TILs (FIG. 12). Of note, TNF deficiency did not impair chemokine mRNA levels in tumors upon anti-PD-1 therapy (data not shown). Collectively, our data indicate that TIL accumulation in TNF-deficient mice resulted from an increased TIL survival rather than an increase in T cell proliferation or chemotaxis under anti-PD-1 therapy.

Example 8

TNF Deficiency Enhances IFN-γ Response and Reduces PD-L1 Expression.

In WT mice, anti-PD-1 injection elicited an increased expression of both TNF and IFN-γ transcripts in tumors (FIGS. 6b and c). Interestingly, in tumors from TNF-deficient mice, IFN-γ transcripts were increased under basal conditions and further enhanced upon anti-PD-1 treatment (FIG. 6c). In tumors from CD8-deficient mice, TNF and IFN-γ mRNA levels remained low under both control and anti-PD-1 conditions, demonstrating that CD8+ T cells are required for potent production of TNF and IFN-γ in this melanoma model (FIGS. 6b and c).

Whereas the proportion of IFN-γ+CD8+ TILs remained unaffected by TNF loss, IFN-γ+CD4+ TILs were significantly increased, arguing that TNF limits Th1 response under anti-PD-1 therapy (data not shown). Thus, the increased expression of IFN-γ in tumors from TNF-deficient mice was associated with an enhanced Th1 polarization and the accumulation of CD8+ TILs, which are potent producers of IFN-γ. The proportion of granzyme B+CD8+ TILs was also significantly increased in TNF-deficient mice (data not shown), indicating that TNF impairs the accumulation of cytotoxic CD8+ TILs.

TNF is known to promote PD-L1 expression in solid cancers[17], including melanoma[15]. We then analyzed PD-L1 and PD-L2 levels under our experimental conditions. In WT mice, treatment with anti-PD-1 selectively enhanced PD-L1, but not PD-L2, expression on both CD4+ and CD8+ TILs (FIG. 13a and data not shown). TNF deficiency totally abrogated PD-L1 up-regulation on TILs upon anti-PD-1 therapy (FIG. 13a). We also monitored the tumor content of dendritic cells (DC), which play a key role in the priming of T cells. Tumor-infiltrating DC were slightly, yet significantly, increased in WT mice treated with anti-PD-1 as well as in TNF-deficient mice with or without anti-PD-1 injection (FIG. 13b). Moreover, the expression of PD-L1 and, albeit to a lesser extent, PD-L2 was reduced on DC in TNF-deficient mice under control and anti-PD-1 conditions (FIGS. 13c and 13d). Thus, TNF deficiency favors DC accumulation in tumors, while reducing, but not abrogating, their expression of the PD-1 ligands.

Example 9

TNF Enhances TIM-3 Expression on Tumor-Infiltrating Leukocytes.

TIM-3 inhibits Th1 responses and triggers peripheral tolerance[28]. This newly recognized key immune checkpoint molecule impairs the antigen-specific CD8+ T cell response in melanoma[29] and plays a major role in the immune escape mechanisms. This was associated with resistance of melanoma to anti-PD-1 both in mice and patients[22].

We assessed TIM-3 expression on TILs and found that over 70% of CD8+ TILs and 50% of CD4+ TILs co-expressed PD-1 and TIM-3, irrespectively of the TNF status (FIG. 11). The mean fluorescence intensity (MFI) of TIM-3 staining, which reflects its expression on TILs, was significantly increased on CD8+ and CD4+ TILs following anti-PD-1 administration in WT mice (FIG. 4D). In sharp contrast, the TIM-3 up-regulation was totally abolished in TNF-deficient mice (FIG. 4D), suggesting that the anti-PD-1-triggered TIM-3 expression occurred in a TNF-dependent manner. Of note, TNF-deficiency did not impair the expression of TIGIT, LAG3 and CTLA-4 on CD8+ TILs (data not shown), indicating that TNF is unlikely a potent inducer of those immune checkpoints under our experimental conditions.

To evaluate whether TNF can induce TIM-3 expression, we purified and activated naive murine CD8+ T cells prior to incubation with exogenous and sub-toxic doses of murine TNF. TNF elicited an increase of both the percentage of TIM-3+CD8+ T cells and the MFI of TIM-3 staining (FIG. 4E). This was suppressed in TNFR1-deficient CD8+ T cells, indicating that TNF induced TIM-3 expression in a TNFR1-dependent manner (data not shown). Accordingly, TNF failed to trigger TIM-3 expression on non-activated CD8+ T cells, which do not express TNFR1[14] (data not shown). Whereas TNF potently upregulated TIM-3 expression on activated CD8+ T cells, it had no or minimal effect on TIGIT and LAG3 expression (data not shown). Of interest, TNF also stimulated the expression of TIM-3 on purified naive and activated human CD8+ T cells (data not shown).

We next investigated the molecular mechanisms involved in TNF-induced TIM-3 expression on activated CD8+ T cells. We focused our analysis on the signaling pathways, i.e., MEK, p38 MAPK and PI3K, which are activated by TNF[30], and lead to TIM-3 expression[31,32]. Pharmacological inhibition of PI3K and MEK, but not p38 MAPK, significantly reduced basal TIM-3 expression. Interestingly, only the p38 MAPK inhibitor totally prevented TNF-induced TIM-3 expression on activated CD8+ T cells (data not shown). Thus, p38 MAPK likely plays a critical role in TIM-3 up-regulation on CD8+ T cells in response to TNF.

Example 10

Anti-TNF Antibodies Synergize with Anti-PD-1 Therapy.

To evaluate the therapeutic relevance of the above observations, we tested the combination of anti-TNF and anti-PD-1 blocking antibodies in mouse melanoma (FIG. 3a). As compared to untreated mice, anti-TNF alone slightly inhibited B16K1 melanoma growth (FIGS. 3B and C). Interestingly, combining anti-PD-1 and anti-TNF led to a total regression of 75% of the tumors (FIGS. 3B and C) and led to the survival of 75% of mice as compared to less than 20% in the group of mice injected with anti-PD-1 alone (FIG. 3D). Surviving mice were totally vaccinated against B16K1 (data not shown). Of note, anti-TNF and anti-TNFR1 also synergised with anti-PD-1 in a breast cancer model based on orthotopic graft of 4T1 cells in the mammary fat pad of Balb/c mice. Whereas anti-PD-1, anti-TNF or anti-TNFR1 alone failed to impair tumor growth, anti-PD-1 and anti-TNF combination or anti-PD-1 and anti-TNFR1 combination significantly decreased it (FIG. 14).

To further investigate the molecular and cellular mechanisms involved in the therapeutic benefit of combining anti-PD-1 and anti-TNF, we analysed the CD8+ TILs in B16K1 tumors. Anti-TNF augmented the proportion of CD8+ TILs (FIG. 6O and prevented not only their death (data not shown) but also their up-regulation of TIM-3 (FIGS. 15a and 15b) in response to anti-PD-1 treatment. These findings show that TNF produced upon anti-PD-1 therapy triggers both AICD of CD8+ TILs and TIM-3 up-regulation on TILs. We next compared the efficacy of a therapy that includes anti-PD-1 as a backbone on established tumors and tested various combinations with the first antibody injection delayed to day 13. Co-administrations of anti-TIM-3 and anti-TNF were equally effective in reducing tumor growth (FIGS. 15c and 15d). Finally, co-injecting anti-TIM-3 together with anti-TNF and anti-PD-1 did not further improve the therapeutic effect (FIGS. 15c and 15d). Similar findings were observed in TNF-deficient mice, in which anti-TIM-3 injection did not enhance anti-PD-1 therapeutic effects (data not shown). Altogether, the data indicate that the therapeutic benefit of combining anti-TNF and anti-PD-1 is, at least in part, due to the inhibition of the TIM-3-dependent pathway.

Example 11

A High TNF Expression is Associated with Immune Escape Gene Signature in Human Melanoma.

To evaluate how our findings translate to metastatic melanoma in patients, we next analysed the TCGA melanoma data bank[33] for the expression of a set of genes encoding proteins involved in immune escape and, eventually, resistance to anti-PD-1 therapy.

Strikingly, an immune escape gene signature is enriched in melanoma samples exhibiting high TNF expression, suggesting that TNF is part of a gene network, which leads to immune suppression in human melanoma (data not shown).

In addition, the expression of TNFA (encoding TNF) positively and significantly correlated with that of HAVCR2 (encoding TIM-3), PDCD1LG1 (encoding PD-L1) and PDCD1LG2 (encoding PD-L2) (FIG. 7 and data not shown). Our analysis of another published dataset[23] also revealed a strong positive and significant correlation between TNFA, HAVCR2, PDCD1LG1 and PDCD1LG2 expression in melanoma specimens from patients treated with anti-PD-1 (data not shown).

Thus, along with our preclinical data, those observations on human melanoma suggest that TNF potently induces the expression of PD-L1, PD-L2 and TIM-3 in melanoma upon anti-PD-1 therapy.

REFERENCES

Throughout this application, various references describe the state of the art to which this invention pertains. The disclosures of these references are hereby incorporated by reference into the present disclosure.

1. Bertrand, F., Colacios, C. & Segui, B. TNF-R1, an immune checkpoint in melanoma? *Genes Cancer* 6, 369-370 (2015).
2. Bertrand, F., et al. Targeting TNF alpha as a novel strategy to enhance CD8+ T cell-dependent immune response in melanoma? *Oncoimmunology* 5, e1068495 (2016).
3. Balkwill, F. Tumour necrosis factor and cancer. *Nat Rev Cancer* 9, 361-371 (2009).
4. Carswell, E. A., et al. An endotoxin-induced serum factor that causes necrosis of tumors. *Proc Natl Acad Sci USA* 72, 3666-3670 (1975).
5. Ratner, A. & Clark, W. R. Role of TNF-alpha in CD8+ cytotoxic T lymphocyte-mediated lysis. *J Immunol* 150, 4303-4314 (1993).
6. Chopra, M., et al. Tumor necrosis factor receptor 2-dependent homeostasis of regulatory T cells as a player in TNF-induced experimental metastasis. *Carcinogenesis* 34, 1296-1303 (2013).
7. Okubo, Y., Mera, T., Wang, L. & Faustman, D. L. Homogeneous expansion of human T-regulatory cells via tumor necrosis factor receptor 2. *Sci Rep* 3, 3153 (2013).
8. Schioppa, T., et al. B regulatory cells and the tumor-promoting actions of TNF-alpha during squamous carcinogenesis. *Proc Natl Acad Sci USA* 108, 10662-10667 (2011).
9. Zhao, X., et al. TNF signaling drives myeloid-derived suppressor cell accumulation. *J Clin Invest* 122, 4094-4104 (2012).
10. Sade-Feldman, M., et al. Tumor necrosis factor-alpha blocks differentiation and enhances suppressive activity of immature myeloid cells during chronic inflammation. *Immunity* 38, 541-554 (2013).
11. Beyer, M., et al. Tumor-necrosis factor impairs CD4(+) T cell-mediated immunological control in chronic viral infection. *Nat Immunol* 17, 593-603 (2016).
12. Chen, X., Baumel, M., Mannel, D. N., Howard, O. M. & Oppenheim, J. J. Interaction of TNF with TNF receptor type 2 promotes expansion and function of mouse CD4+ CD25+T regulatory cells. *J Immunol* 179, 154-161 (2007).
13. Zheng, L., et al. Induction of apoptosis in mature T cells by tumour necrosis factor. *Nature* 377, 348-351 (1995).
14. Bertrand, F., et al. Blocking Tumor Necrosis Factor alpha Enhances CD8 T-cell-Dependent Immunity in Experimental Melanoma. *Cancer Res* 75, 2619-2628 (2015).
15. Donia, M., et al. Aberrant Expression of MHC Class II in Melanoma Attracts Inflammatory Tumor-Specific CD4+ T-Cells, Which Dampen CD8+ T-cell Antitumor Reactivity. *Cancer Res* 75, 3747-3759 (2015).
16. Landsberg, J., et al. Melanomas resist T-cell therapy through inflammation-induced reversible dedifferentiation. *Nature* 490, 412-416 (2012).
17. Lim, S. O., et al. Deubiquitination and Stabilization of PD-L1 by CSN5. *Cancer Cell* 30, 925-939 (2016).
18. Larkin, J., et al. Combined Nivolumab and Ipilimumab or Monotherapy in Untreated Melanoma. *N Engl J Med* 373, 23-34 (2015).
19. Robert, C., et al. Nivolumab in previously untreated melanoma without BRAF mutation. *N Engl J Med* 372, 320-330 (2015).
20. Robert, C., et al. Pembrolizumab versus Ipilimumab in Advanced Melanoma. *N Engl J Med* 372, 2521-2532 (2015).
21. Postow, M. A., Callahan, M. K. & Wolchok, J. D. Immune Checkpoint Blockade in Cancer Therapy. *J Clin Oncol* 33, 1974-1982 (2015).
22. Koyama, S., et al. Adaptive resistance to therapeutic PD-1 blockade is associated with upregulation of alternative immune checkpoints. *Nat Commun* 7, 10501 (2016).
23. Chen, P. L., et al. Analysis of Immune Signatures in Longitudinal Tumor Samples Yields Insight into Biomarkers of Response and Mechanisms of Resistance to Immune Checkpoint Blockade. *Cancer Discov* 6, 827-837 (2016).
24. Spain, L., Diem, S. & Larkin, J. Management of toxicities of immune checkpoint inhibitors. *Cancer Treat Rev* 44, 51-60 (2016).
25. Tumeh, P. C., et al. PD-1 blockade induces responses by inhibiting adaptive immune resistance. *Nature* 515, 568-571 (2014).
26. Rizvi, N. A., et al. Activity and safety of nivolumab, an anti-PD-1 immune checkpoint inhibitor, for patients with advanced, refractory squamous non-small-cell lung cancer (CheckMate 063): a phase 2, single-arm trial. *Lancet Oncol* 16, 257-265 (2015).
27. Borghaei, H., et al. Nivolumab versus Docetaxel in Advanced Nonsquamous Non-Small-Cell Lung Cancer. *N Engl J Med* 373, 1627-1639 (2015).
28. Sabatos, C. A., et al. Interaction of Tim-3 and Tim-3 ligand regulates T helper type 1 responses and induction of peripheral tolerance. *Nat Immunol* 4, 1102-1110 (2003).
29. Fourcade, J., et al. Upregulation of Tim-3 and PD-1 expression is associated with tumor antigen-specific CD8+ T cell dysfunction in melanoma patients. *J Exp Med* 207, 2175-2186 (2010).
30. Borghi, A., Verstrepen, L. & Beyaert, R. TRAF2 multitasking in TNF receptor-induced signaling to NF-kappaB, MAP kinases and cell death. *Biochem Pharmacol* 116, 1-10 (2016).
31. Yoon, S. J., et al. Activation of mitogen activated protein kinase-Erk kinase (MEK) increases T cell immunoglobulin mucin domain-3 (TIM-3) transcription in human T lymphocytes and a human mast cell line. *Mol Immunol* 48, 1778-1783 (2011).
32. Mujib, S., et al. Antigen-independent induction of Tim-3 expression on human T cells by the common gamma-chain cytokines IL-2, IL-7, IL-15, and IL-21 is associated with proliferation and is dependent on the phosphoinositide 3-kinase pathway. *J Immunol* 188, 3745-3756 (2012).

33. Cancer Genome Atlas, N. Genomic Classification of Cutaneous Melanoma. *Cell* 161, 1681-1696 (2015).
34. Daud, A. I., et al. Tumor immune profiling predicts response to anti-PD-1 therapy in human melanoma. *J Clin Invest* 126, 3447-3452 (2016).
35. Sakuishi, K., et al. Targeting Tim-3 and PD-1 pathways to reverse T cell exhaustion and restore anti-tumor immunity. *J Exp Med* 207, 2187-2194 (2010).
36. Ngiow, S. F., et al. Anti-TIM3 antibody promotes T cell IFN-gamma-mediated antitumor immunity and suppresses established tumors. *Cancer Res* 71, 3540-3551 (2011).
37. Zhu, C., et al. An IL-27/NFIL3 signalling axis drives Tim-3 and IL-10 expression and T-cell dysfunction. *Nat Commun* 6, 6072 (2015).
38. Galluzzi, L., et al. Essential versus accessory aspects of cell death: recommendations of the NCCD 2015. *Cell Death Differ* 22, 58-73 (2015).
39. Porgador, A., Feldman, M. & Eisenbach, L. H-2Kb transfection of B16 melanoma cells results in reduced tumourigenicity and metastatic competence. *J Immunogenet* 16, 291-303 (1989).
40. Pequeux, C., et al. Stromal estrogen receptor-alpha promotes tumor growth by normalizing an increased angiogenesis. *Cancer Res* 72, 3010-3019 (2012).
41. Sheehan, K. C., et al. Monoclonal antibodies specific for murine p55 and p75 tumor necrosis factor receptors: identification of a novel in vivo role for p75. *J Exp Med* 181, 607-617 (1995).

The invention claimed is:

1. A method of treating cancer in a subject in need thereof, comprising
co-administering to the subject a therapeutically effective amount of a combination of
an immune checkpoint inhibitor, wherein the immune checkpoint inhibitor is an antibody inhibitor of programmed cell death protein-1 (PD-1) selected from the group consisting of nivolumab and pembrolizumab, with
a tumor necrosis factor-alpha (TNFα) blocking agent, wherein the TNFα blocking agent is an antibody having specificity for TNFα or TNFα receptor 1 (TNFR1) selected from the group consisting of certolizumab pegol, etanercept, infliximab, adalimumab, and golimumab,
wherein a dosing regimen of the therapeutically effective amount comprises at least one co-administration of at least 10 mg/kg of the immune checkpoint inhibitor and at least 10 mg/kg of the TNFα blocking agent,
wherein co-administration of the combination results in enhanced therapeutic efficacy relative to the administration of the immune checkpoint inhibitor alone,
wherein said cancer is selected from the group consisting of melanoma, breast cancer and lung cancer, and
wherein said therapeutic efficacy is indicated by regression of a tumor of the cancer.

2. The method of claim 1, wherein the cancer is melanoma, and the dosing regimen comprises at least three co-administrations of at least 10 mg/kg of the immune checkpoint inhibitor and at least 10 mg/kg of the TNFα blocking agent delivered at intervals of three to four days.

3. The method of claim 1, wherein the subject suffers from a melanoma resistant to BRAF inhibitors.

4. The method of claim 1, wherein the anti-PD-1 antibody is nivolumab.

5. The method of claim 1, wherein the TNFα blocking agent is certolizumab pegol.

6. A method of treating melanoma in a subject in need thereof, comprising
co-administering to the subject a therapeutically effective amount of a combination of
an immune checkpoint inhibitor anti-programmed cell death protein-1 (anti-PD-1) antibody selected from the group consisting of nivolumab and pembrolizumab, with
an anti-tumor necrosis factor-alpha (TNFα) antibody, wherein the anti-TNFα antibody is selected from the group consisting of certolizumab pegol, etanercept, infliximab, adalimumab, and golimumab,
wherein the dosing regimen comprises at least three co-administrations of at least 10 mg/kg of the immune checkpoint inhibitor and at least 10 mg/kg of the TNFα blocking agent delivered at intervals of three to four days,
wherein administration of the combination results in enhanced therapeutic efficacy relative to the administration of the immune checkpoint inhibitor alone, and
wherein said therapeutic efficacy is indicated by regression of a tumor of the cancer.

7. The method of claim 6, wherein the anti-PD-1 antibody is nivolumab.

8. The method of claim 6, wherein the anti-TNFα antibody is certolizumab pegol.

* * * * *